United States Patent
Pham et al.

(10) Patent No.: US 8,899,482 B2
(45) Date of Patent: Dec. 2, 2014

(54) DIGITAL MEASUREMENT SYSTEM WITH MAGNETIC CARD READER AND METHOD FOR OPTICAL APPLICATIONS

(71) Applicant: VSP Labs, Inc., Rancho Cordova, CA (US)

(72) Inventors: Mai Ngoc Pham, Elk Grove, CA (US); Hoa Dang Nguyen, Cider Hills, TX (US)

(73) Assignee: VSP Labs, Inc., Rancho Cordova, CA (US)

( * ) Notice: Subject to any disclaimer, the term of this patent is extended or adjusted under 35 U.S.C. 154(b) by 250 days.

(21) Appl. No.: 13/630,518

(22) Filed: Sep. 28, 2012

(65) Prior Publication Data

US 2013/0278896 A1    Oct. 24, 2013

Related U.S. Application Data

(63) Continuation-in-part of application No. 13/454,163, filed on Apr. 24, 2012.

(51) Int. Cl.
*A61B 3/10* (2006.01)
(52) U.S. Cl.
USPC ........... 235/449; 235/375; 351/204; 424/447; 424/613

(58) Field of Classification Search
USPC ............ 235/449, 375; 351/204; 424/447, 613
See application file for complete search history.

(56) References Cited

U.S. PATENT DOCUMENTS

| | | | |
|---|---|---|---|
| 2004/0004633 A1 | 1/2004 | Perry et al. | |
| 2006/0132485 A1* | 6/2006 | Milinusic | 345/419 |
| 2010/0150991 A1* | 6/2010 | Bernstein | 424/447 |
| 2011/0242481 A1 | 10/2011 | Wada | |
| 2013/0060241 A1* | 3/2013 | Haddad | 606/4 |
| 2014/0192316 A1* | 7/2014 | Krenik | 351/203 |

* cited by examiner

Primary Examiner — Allyson Trail
(74) Attorney, Agent, or Firm — Brient Globerman LLC

(57) ABSTRACT

A digital measurement system and method for optical applications including a mobile client device having a digital camera and an audio port, and a laser measurement device having a laser and a magnetic card reader. The laser measurement device and the magnetic card reader are electrically connected to the audio port of the mobile client device. The mobile client device is configured to activate the laser at the same time as the digital camera is activated, capture an image of a patient, and calculate position of wear measurements based on a location of a laser mark in the captured image. The mobile client device also allows an order for a frame and lenses to be submitted to a ophthalmic laboratory, and payment transactions to be processed using the magnetic card reader.

20 Claims, 17 Drawing Sheets

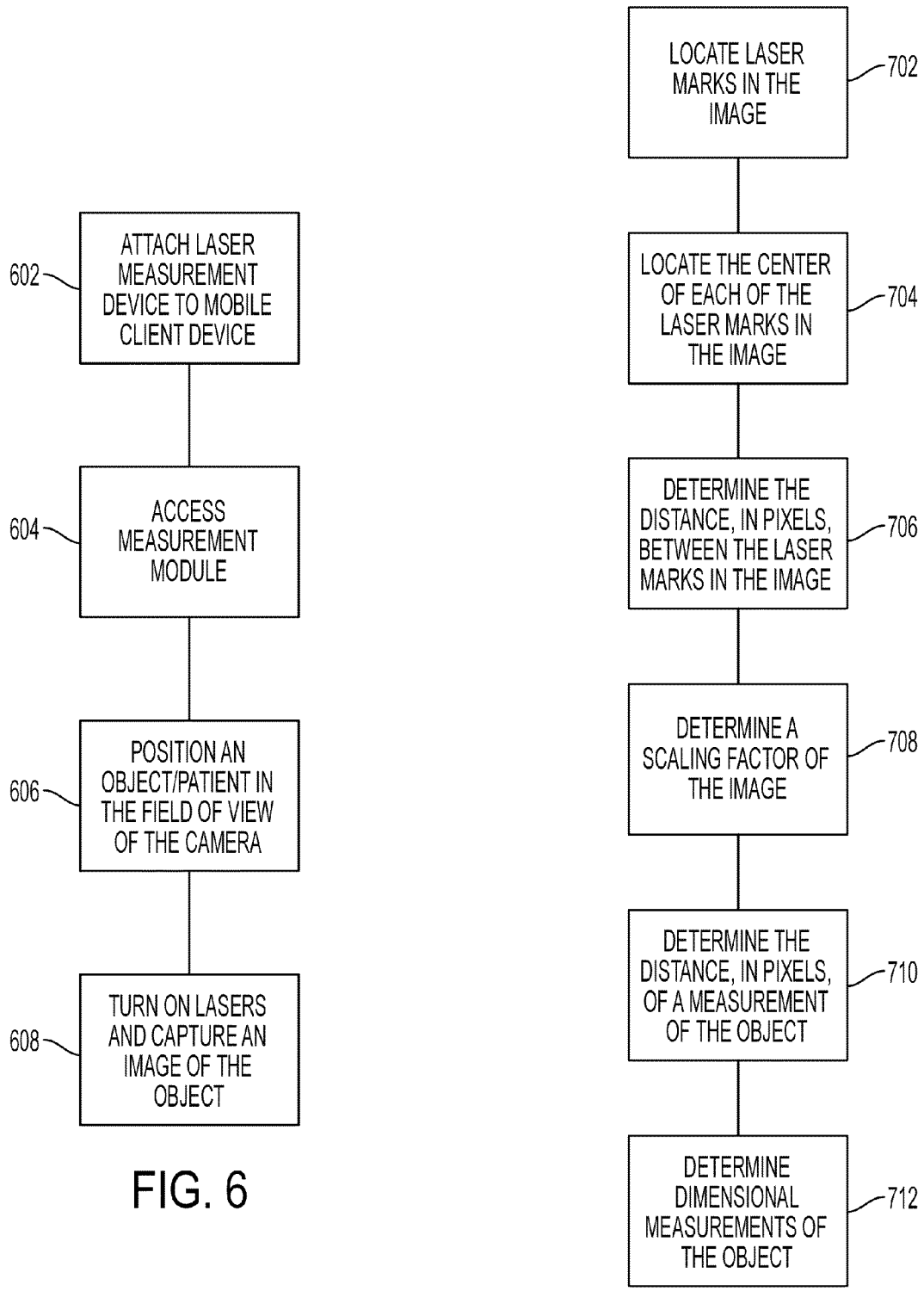

DIGITAL MEASUREMENT SYSTEM WITH MAGNETIC CARD READER AND METHOD FOR OPTICAL APPLICATIONS

CROSS REFERENCES TO RELATED APPLICATIONS

This application is a Continuation-in-Part (CIP) application of and claims the benefit of U.S. patent application Ser. No. 13/454,163 filed on Apr. 24, 2012, the contents of which are incorporated herein by reference in their entirety.

FIELD

The disclosure generally relates to eye care. More specifically, the disclosure relates to patient measurements for optical devices.

BACKGROUND

In general, eye care professionals (ECPs) prescribe lenses, fit lenses, and dispense prescriptions for eye correction to improve vision and to diagnose and treat various eye maladies. Lens prescriptions are typically determined using a refractor-head or test lenses that are positioned perpendicular to a patient's lines of sight. However, when the patient chooses a frame and the frame is fitted to the patient, the lenses are usually tilted based on the position of the frame. This tilt of the lenses can result in the prescription power being altered.

With the introduction of free form surfacing, also known as direct or digital surfacing, prescription lenses can be customized to a particular patient. Free form surfacing allows for complex surface shapes to be produced using computer numerically controlled (CNC) cutting tools and polishing machines.

Through the use of free form surfacing combined with accurate position of wear measurements, lenses can be customized to the patient's prescription, fitting geometry, and frame information. The position of wear is the position of the lens relative to the physical features of the actual patient. The position of wear is commonly measured in terms of vertex distance, pupillary distance, frame wrap, and pantoscopic tilt.

These measurements are generally taken using manual devices such as rulers, protractor type devices, distometers, and other manual devices or digital measurement devices. Current digital measurement devices are generally large stand alone devices that require the use of a separate reference sensor. In general, the current digital measurement devices require the patient's frames to be fit to the patient and the reference sensor must be positioned correctly on the fitted frames. If the reference sensor is not correctly positioned on the fitted frames, the measurement accuracy can be compromised.

SUMMARY

The digital measurement system and method for optical applications disclosed herein provides a mobile client device for obtaining patient measurements and/or position of wear measurements. The mobile client device may be implemented within and connected to a network of computer systems, for example, in a cloud computing infrastructure. This allows the mobile client device to access a measurement module and one or more databases to perform various functions, including calculating and determining measurements based on an image of a patient wearing a frame without using a reference sensor connected to the frame.

In an illustrative embodiment, the system includes a mobile client device in communication with a computing infrastructure allowing the mobile client device to access a measurement module. The mobile client device includes a digital camera and an audio port. A laser measurement device having a laser is connected to the mobile client device, and electrically connected to the audio port of the mobile client device. The mobile client device is configured to activate the laser, for example, by transmitting an audio signal via the audio port to the laser measurement device, when the digital camera is activated to capture an image including a mark made by the laser within the image.

The laser measurement device may include a first laser and a second laser. The first laser and the second laser are positioned parallel with respect to one another a fixed distance apart. In an illustrative embodiment, the laser measurement device is positioned on a top portion of the mobile client device with the first laser and the second laser positioned on opposite sides of the digital camera.

In an illustrative embodiment, a method for obtaining digital measurements includes sending, by a mobile client device, an audio signal to activate a laser and capturing, by the mobile client device, an image of a patient wearing a selected frame at the same time as the laser is activated. The mobile client device accesses a measurement module. The measurement module is configured to analyze the captured image and determine a position of wear measurement, for example, a monocular pupillary distance (PD), a binocular PD, a monocular near PD, a binocular near PD, a vertex distance, a pantoscopic tilt, and other measurements of the type of the patient wearing the selected frame based on a location of a mark made by the laser in the captured image. The mobile client device may also store the position of wear measurement in a database.

In an illustrative embodiment, the mobile client device may submit an order for a frame and lenses to an ophthalmic laboratory including the position of wear measurement(s). The ophthalmic laboratory may use the position of wear measurement(s) to produce customized lenses for the patient.

In an illustrative embodiment, a method for obtaining digital measurements for optical applications includes locating, by a measurement module, a first laser mark created by a first laser and a second laser mark created by a second laser within a digital image. The measurement module determines a distance between the first laser mark and the second laser mark, in terms of a number of pixels. Since an actual distance between the first laser and the second laser is fixed, the measurement module determines a scaling factor for the digital image using the actual distance between the first laser and the second laser and the distance, in pixels, between the first laser mark and the second laser mark. Using the scaling factor, the measurement module determines one or more positions of wear measurements of a patient from the digital image.

In an illustrative embodiment, the measurement module determines a monocular PD of the patient by determining a distance in pixels between an eye of the patient and a bridge of a nose of the patient in the digital image and multiplying the distance, in pixels, by the scaling factor. The measurement module determines a binocular PD of the patient by determining a distance in pixels between a center of each eye of the patient in the digital image, and multiplying the distance, in pixels, by the scaling factor. The measurement module determines a vertex distance by determining a distance in pixels between a back surface of a lens being worn by the patient and a front of a cornea of the patient in the digital image, and multiplying the distance, in pixels, by the scaling factor. The measurement module determines a pantoscopic tilt by determining an angle between a plane of a frame front and a frontal plane of a face of the patient in the digital image using distance measurements and calculations of a triangle.

In an illustrative embodiment, the measurement module determines a distance between a patient and a digital camera used to capture an image of the patient. On one embodiment, the distance is determined based on a focal length of the digital camera, a horizontal pixel position of a first mark made by a laser in the captured image, and the actual distance between the laser and the digital camera.

In another illustrative embodiment, a laser measurement device including a magnetic card reader is disclosed herein. The magnetic card reader provides the capability to process credit card transactions. This allows the digital measurement system to process payment associated with the submission of the order for the frame and lenses to the ophthalmic laboratory via the mobile client device and other transactions.

BRIEF DESCRIPTION OF THE DRAWINGS

The systems and methods disclosed herein are illustrated in the figures of the accompanying drawings which are meant to be exemplary and not limiting, in which like references are intended to refer to like or corresponding parts, and in which:

FIG. 6 illustrates a method of using the mobile client device and the laser measurement device;

FIG. 7 illustrates a flow diagram of a method for obtaining dimensional measurements;

DETAILED DESCRIPTION

Detailed embodiments of a digital measurement system and method for optical applications are disclosed herein, however, it is to be understood that the disclosed embodiments are merely exemplary of the systems and methods, which may be embodied in various forms. Therefore, specific functional details disclosed herein are not to be interpreted as limiting, but merely as a basis for the claims and as a representative basis for teaching one skilled in the art to variously employ the systems and methods disclosed herein.

Generally, the systems and methods disclosed herein include and are implemented within a computer system, network of computer systems, and/or cloud computing infrastructure having one or more databases and other storage apparatuses, servers, computers, and additional components, for example, processors, modems, terminals and displays, computer-readable media, algorithms, modules, and other computer-related components. The computer systems and/or computing infrastructure are especially configured, programmed, and adapted to perform the functions and processes of the systems and methods as disclosed herein.

Communications between components in the systems and methods disclosed herein may be unidirectional or bidirectional electronic communication through a wired or wireless configuration or network. For example, one component may be wired or networked directly, indirectly, through a third party intermediary, wirelessly, over the Internet, or otherwise with another component to enable communication between the components.

Figure 1:
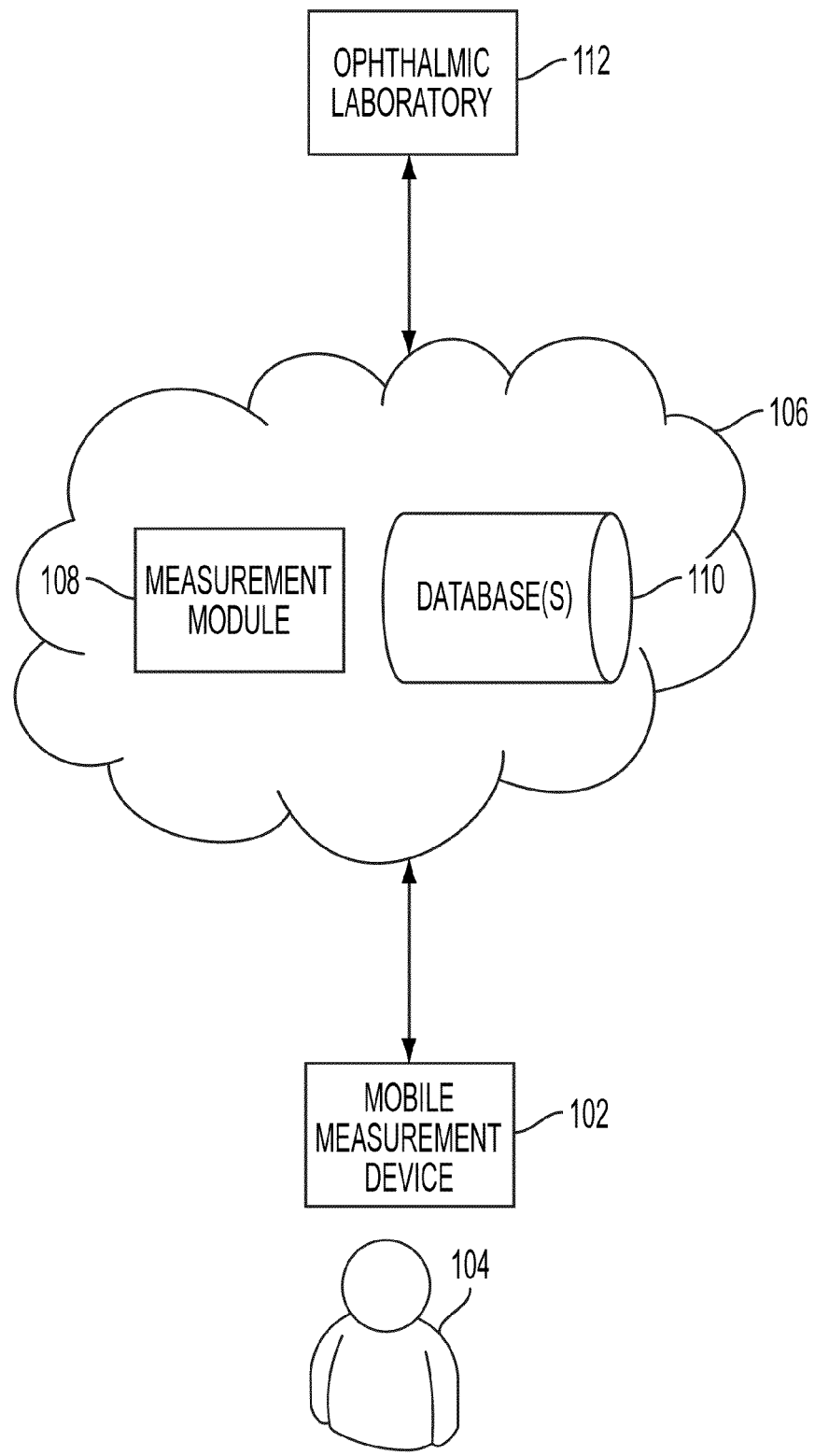
FIG. 1 illustrates an overview of the digital measurement system and method for optical applications.

An overview of the digital measurement system and method for optical applications according to an illustrative embodiment is described with reference to FIG. 1. As illustrated in FIG. 1, the system includes at least one mobile client device 102 configured to receive or collect data of or from at least one user 104, which may be a patient or an eye care professional (ECP), for example, an optometrist, an optician, an assistant, or other eye care technician. The mobile client device 102 includes an optical system and image acquisition technology. The optical system and image acquisition technology may be one or more digital cameras or digital video recorders capable of collecting one or more images, videos, or taking one or more photographs.

In an illustrative embodiment, the mobile client device 102 communicates with, accesses, receives data from, and transmits data to a computing infrastructure 106. In general, the computing infrastructure 106 provides computing/processing resources, software, data access, and storage resources without requiring the user or client to be familiar with the location and other details of the computing infrastructure 106. The computing infrastructure 106 includes one or more modules accessible by the mobile client device 102, including a measurement module 108 and one or more associated databases 110. In an illustrative embodiment, the mobile client device 102 may communicate with one or more ophthalmic laboratories 112 via the computing infrastructure 106 to submit orders to the one or more ophthalmic laboratories 112 for frames and/or lenses.

In an illustrative embodiment, the mobile client device 102 accesses the measurement module 108 allowing accurate position of wear measurements of a patient to be obtained based on one or more images of the patient. The mobile client device 102 can be used to obtain, for example, monocular pupillary distance (PD), binocular PD, monocular near PD, binocular near PD, vertex distance, wrap angle, pantoscopic tilt, and other measurements of the type. These measurements may then be sent to and used, for example, by the one or more ophthalmic laboratories 112 to produce customized lenses for the patient.

Figure 2A:
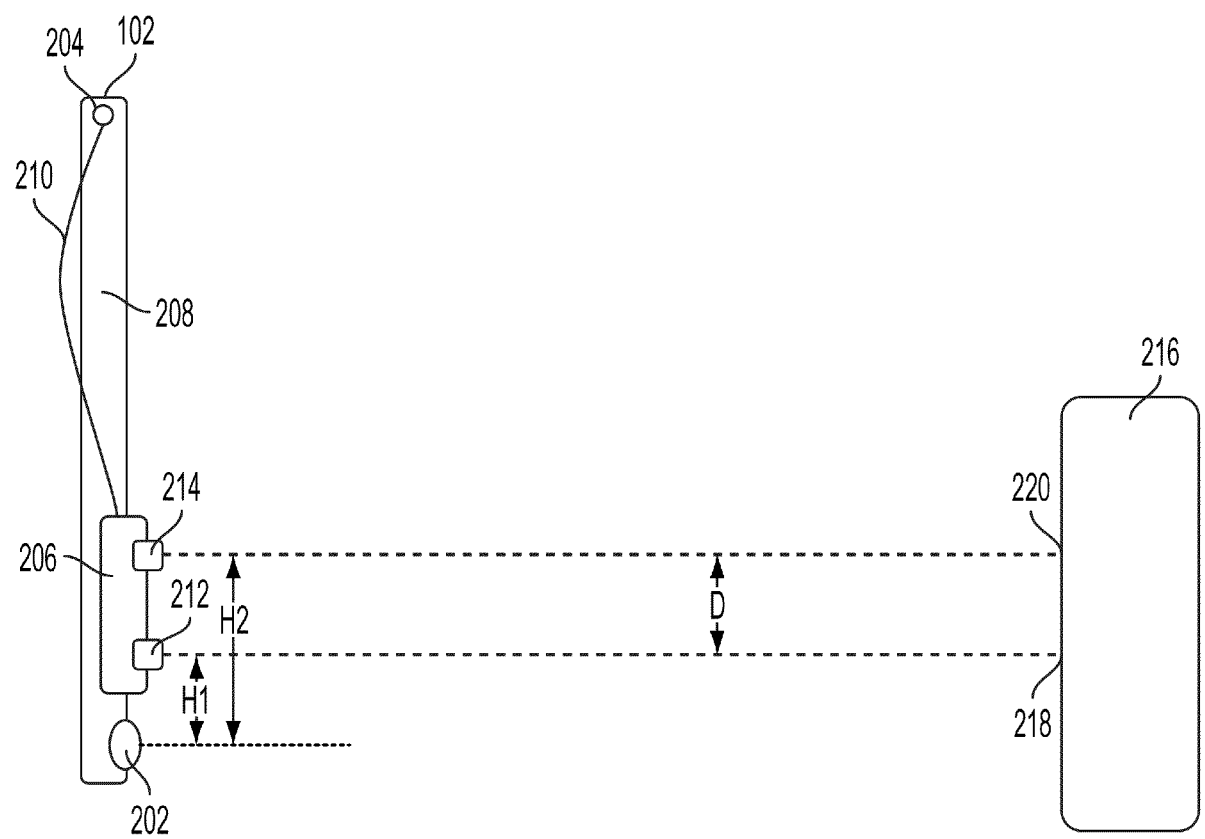
FIG. 2A illustrates a top view of a mobile client device including a laser measurement device of the digital measurement system.
Figure 2B:
FIG. 2B illustrates a side view of the mobile client device including the laser measurement device of the digital measurement system.

A mobile client device 102 according to an illustrative embodiment is described with reference to FIGS. 2A and 2B. As illustrated in FIGS. 2A and 2B, the mobile client device 102 is a tablet computing device. The mobile client device 102 includes one or more digital cameras and/or digital video recorders 202. The mobile client device 102 also includes one or more audio ports 204. The one or more audio ports 204 may be, for example, 3.5-mm stereo headphone minijacks, and other audio ports of the type.

In an illustrative embodiment, the mobile client device 102 is an Apple® iPad®, for example, but not limited to a first generation/version, a second generation/version, and other generations/versions of the Apple® iPad®. The Apple® iPad® includes a 3.5-mm stereo headphone minijack (for example, the audio port 204). The second generation Apple® iPad® includes a first digital camera/digital video recorder (for example, the digital cameras and/or digital video recorders 202) on the back of the Apple® iPad®, and a second digital camera/digital video recorder on the front of the Apple® iPad® (not shown). The first digital camera/digital video recorder 202 on the back of the Apple® iPad® is capable of video recording, HD (720p) up to 30 frames per second with audio and has a still camera with 5× digital zoom. The second digital camera/digital video recorder on the front of the Apple® iPad® is capable of video recording, VGA up to 30 frames per second with audio and has a VGA-quality still camera.

In an illustrative embodiment, a laser measurement device 206 is connected to the mobile client device 102. The laser measurement device 206 may be mounted on or removably connected to the mobile client device 102. As illustrated, the laser measurement device 206 is positioned on a first side or a top portion 208 of the mobile client device 102 proximal to the digital camera and/or digital video recorder 202 of the mobile client device 102. The laser measurement device 206 is electrically connected to the mobile client device 102 via the audio port 204. In an illustrative embodiment, the laser measurement device 206 includes wiring 210 including an audio plug configured to be received in and electrically connected to the audio port 204 of the mobile client device 102.

The laser measurement device 206 includes a first visible light, red dot low power laser 212 and a second visible light, red dot low power laser 214. The first and second visible light, red dot low power lasers, 212 and 214, respectively, may be the same lasers or different lasers. In an illustrative embodiment, the first and second lasers 212 and 214, respectively, have a wavelength of about 650 nm and an output power of less than about 1 MW. One example of the first and second lasers 212 and 214, respectively, is part number LC-LMD-650-03-01-A from Laser Components, a distributer and manufacturer of laser products located in Olching, Germany.

As illustrated in FIG. 2A, the first and second lasers 212 and 214, respectively, are spaced apart by a distance D, as measured from the center of the first laser 212 to the center of the second laser 214, and are in parallel alignment with respect to one another. The center of the first laser 212 is positioned a distance H1 from the center of the digital camera and/or digital video recorder 202, and the center of the second laser 214 is positioned a distance H2 from the center of the digital camera and/or digital video recorder 202.

Figure 3:
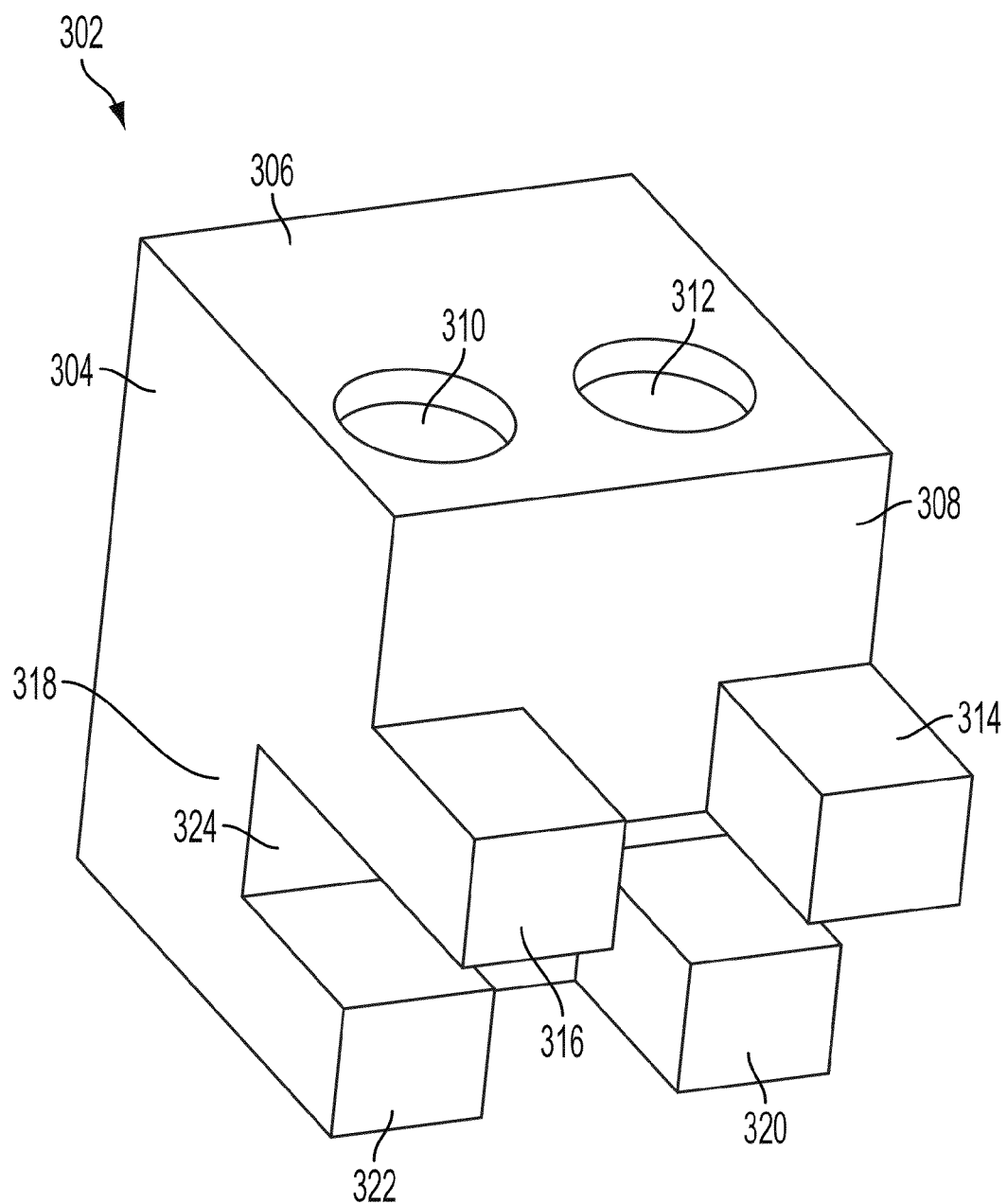
FIG. 3 illustrates an embodiment of a laser measurement device.
Figure 4:
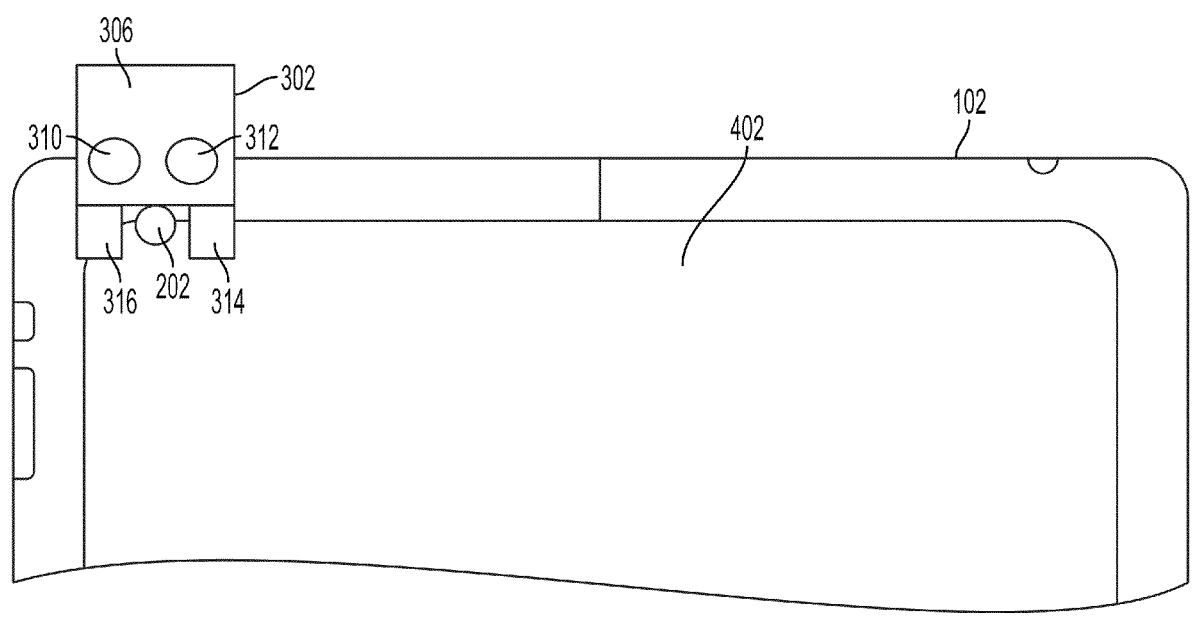
FIG. 4 illustrates an embodiment of the laser measurement device of FIG. 3 attached to the mobile client device.

Another embodiment of a laser measurement device is describe with reference to FIGS. 3 and 4. As illustrated in FIG. 3, a laser measurement device 302 includes an outer housing 304 having a front face 306 and a bottom 308. A first laser 310 and a second laser 312, which may be the same as the first and second lasers 212 and 214, respectively, are positioned within the outer housing 304 on the front face 306 of the laser measurement device 302. As illustrated, the first laser 310 and the second laser 312 are positioned next to each other, horizontally along the front face 306, and are in parallel alignment with one another.

A first support 314 and a second support 316 are attached to or monolithically formed with the outer housing 304 and protrude vertically downward from the bottom 308 or are perpendicular to the bottom 308. As illustrated, the first support 314 and the second support 316 are aligned with one another, horizontally along the bottom 308. The laser measurement device 302 also includes an extended portion 318 attached to or monolithically formed with the outer housing 304 opposite the front face 306 of the outer housing 304. A third support 320 and a fourth support 322 are attached to or monolithically formed with the outer housing 304 and protrude vertically downward from the extended portion 318 or are perpendicular to the extended portion 318. The outer housing 304 and the supports 314, 316, 320, and 322 form a notch 324 between the outer housing 304 and the third support 320 and the fourth support 322, between the first support 314 and the third support 320, and between the second support 316 and the fourth support 322. The laser measurement device 302 also includes wiring including an audio plug configured to be received in and electrically connected to the audio port 204 of the mobile client device 102.

Referring to FIG. 4, the laser measurement device 302 may be placed on the top of the mobile client device 102. As illustrated in FIG. 4, the mobile client device 102 is received in the notch 324 of the laser measurement device 302 and the top of the mobile client device 102 contacts the extended portion 318 of the laser measurement device 302. The first support 314 and the second support 316 engage a back portion 402 of the mobile client device 102 and the third support 320 and the fourth support 322 engage a front portion of the mobile client device 102.

As illustrated in FIG. 4, the laser measurement device 302 is positioned on the mobile client device 102 allowing the digital camera 202 of the mobile client device 102 to be unobstructed. In an illustrative embodiment, the laser measurement device 302 is positioned with the first support 314 and the third support 320 on one side of the digital camera 202 and the second support 316 and the fourth support 322 on an opposite side of the digital camera 202.

In an illustrative embodiment, the first laser 310 and the second laser 312 have a diameter of about 21/64 inches. The front face 306 measures about 1 inch by 1 inch. The length of the outer housing 304 is about 1.5 inches. The length of the extended portion 318 is about 37/64 inches. The first support 314 and the second support 316 extend about 41/64 inches from the bottom 308, and the third support 320 and the fourth support 322 extend about 7/8 inches from the extended portion 318. The recess 324 has a length of about 19/64 inches. The first support 314 and the second support 316, and the third support 320 and the fourth support 322 are spaced apart by a distance of about 0.3 to about 0.4 inches, to allow for the digital camera 202 of the mobile client device 102 to be positioned therebetween.

Although, the laser measurement device 302 is described as having certain dimensions, it should be appreciated by those skilled in the art that the various dimensions may be modified accordingly, for example, increased or decreased, to adapt the laser measurement device to various mobile client devices 102 and various other applications.

The laser measurement devices 206 and 302 also include control circuitry enclosed within an outer housing of the laser measurement devices 206 and 302 for controlling the first laser 212/310 and the second laser 214/312. In an illustrative embodiment, the laser measurement device 206/302 is activated by receiving an audio signal from the mobile client device 102 via the audio port 204. A circuit diagram of the control circuitry of the laser measurement device 206/302 according to an illustrative embodiment is described with reference to FIG. 5. The mobile client device 102 controls the laser measurement device 206/302 by sending a signal, for example, a 10 khz sine wave, through the audio port 204. The laser measurement device 206/302 detects the audio signal and uses the audio signal to control the operation of the first laser 212/310 and the second laser 214/312.

Figure 5:
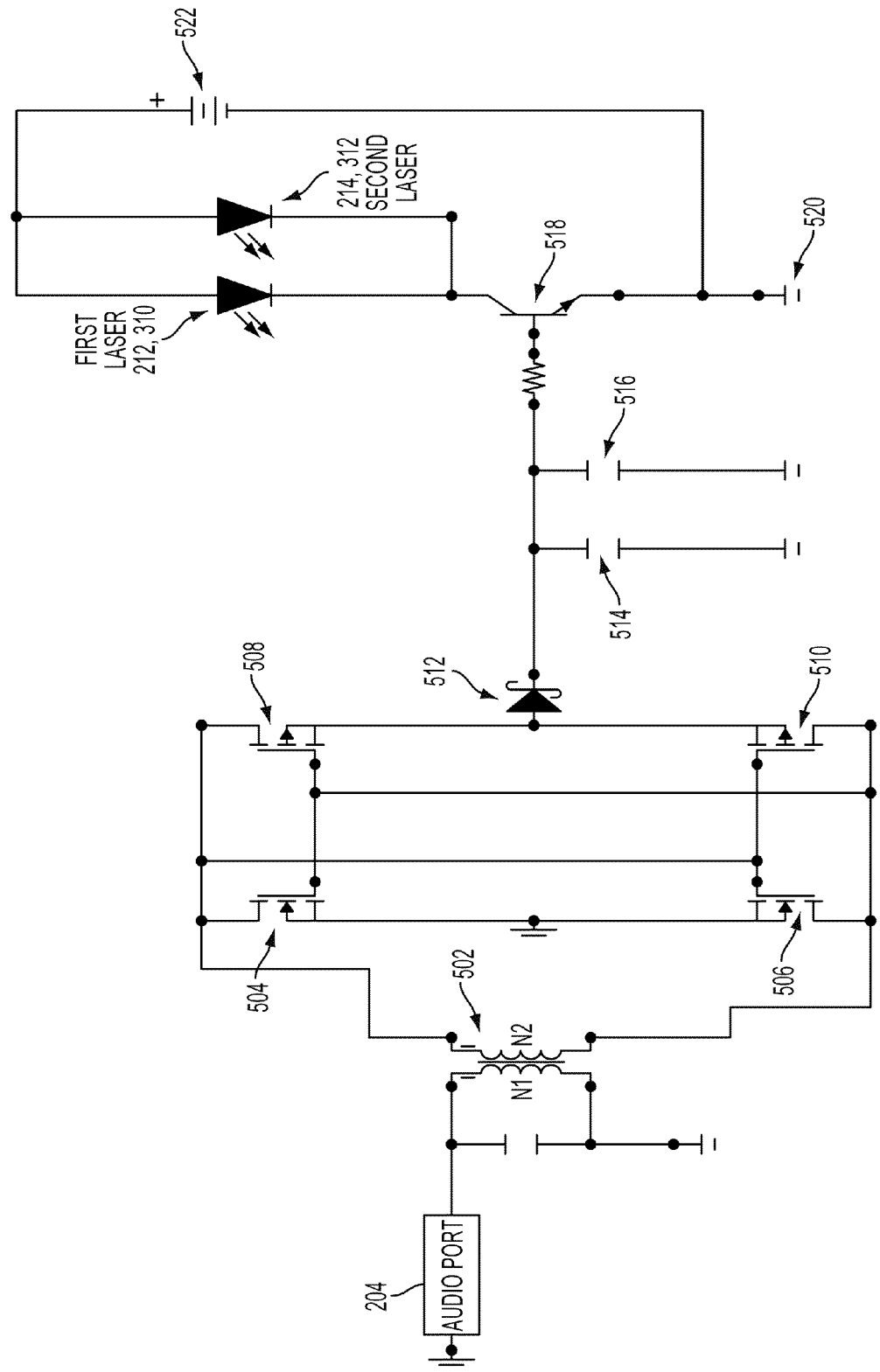
FIG. 5 illustrates a circuit diagram of the laser measurement device of the digital measurement system.

As illustrated in FIG. 5, the signal travels to a transformer 502. The transformer 502 steps up the voltage of the signal. The signal is then rectified by a field-effect transistor (FET) bridge made up of four FETs, 504-510. The rectified signal travels to a blocking diode 512. The blocking diode 512 is used to keep capacitors 514 and 516 from feeding back into the FETs, 504-510. The capacitors 514 and 516 filter the rectified signal into a direct current (DC) voltage. This DC voltage turns on a transistor 518 which activates the first and second lasers (212 and 214) by providing a ground path 520. In an illustrative embodiment, the first laser 212/310 and the second laser 214/312 are powered by a power source 522. In an illustrative embodiment, the power source 522 is, for example, two replaceable LR44 button batteries, however, it should be appreciated by those skilled in the art that the first laser 212/310 and the second laser 214/312 may be powered by one or more additional or alternative batteries, the mobile client device 102, and/or other power sources of the type. Under normal operation the first laser 212/310 and the second laser 214/312 are only activated for a short period of time. When the two replaceable LR44 button batteries are used as the power source 522, the two replaceable LR44 button batteries will generally last about several months to about five years.

A method of using the mobile client device 102 and the laser measurement device 206/302 according to an illustrative embodiment is described with reference to FIGS. 1-4 and 6. As illustrated, the user 104 attaches the laser measurement device 206/302 to the mobile client device 102, illustrated as 602. In an illustrative embodiment, the user 104 attaches the laser measurement device 206/302 to the mobile client device 102 by connecting the laser measurement device 206/302 to the top of the mobile client device 102 and electrically connecting the laser measurement device 206/302 to the mobile client device 102 by connecting the audio plug to the audio port 204 of the mobile client device 102.

The user 104 accesses the measurement module 108 via the mobile client device 102, illustrated as 604. In an illustrative embodiment, the mobile client device 102 is configured to transmit an audio signal, for example, a 10 khz audio signal, via the audio port 204 when the digital camera 202 is activated by the user 104. The laser measurement device 206/302 connected to the audio port 204 receives the audio signal. This causes the laser measurement device 206/302 to turn on for a short period of time, for example, about 100 milliseconds to about 300 milliseconds, when the digital camera 202 is activated in a similar manner as a flash of a camera operates.

The user 104 positions a patient wearing a selected frame or an object, for example, illustrated as 216 in FIGS. 2A and 2B, in the field of view of the digital camera 202, illustrated as 606. The user 104 then simultaneously turns on the laser measurement device 206/302 and captures one or more images of the patient or object on the mobile client device 102, for example, on a screen or display of the mobile client device 102, illustrated as 608. The captured image may be stored, for example, in a memory of the mobile client device 102 and/or in the one or more databases 110. In an illustrative embodiment, the user 104 presses or touches a button on the mobile client device 102 to activate the digital camera 202 and capture the image(s) of the patient or object. When the user 104 activates the digital camera 202, the laser measurement device 206/302 turns on simultaneously as the digital camera 202 captures the image(s). The first laser 212/310 and the second laser 214/312, create a first mark and a second mark, for example, illustrated as 218 and 220 in FIG. 2A, on the patient or object in the captured image.

A method of obtaining dimensional measurements according to an illustrative embodiment is described with reference to FIGS. 1-4 and 7. The measurement module 108 analyzes the captured image(s) and locates the first mark and the second mark created by the first laser 212/310 and the second laser 214/312 within the captured image, 702. The measurement module 108 locates the center of each of the first mark and the second mark created by the first laser 212/310 and the second laser 214/312 within the captured image, 704, using known image processing technology and/or algorithms. In an illustrative embodiment, the measurement module 108 locates the center of each of the first mark and the second mark by filtering and analyzing the captured image. The filtering process involves a combination of Gaussian blur, custom color channel manipulation, intensity thresholding, and a Suzuki85 algorithm for connected component labeling. The filtering process produces a set of points defining possible marks created by the first laser 212/310 and the second laser 214/312 or laser mark candidate shapes. The set of points or shapes is analyzed according to several criteria, such as, but not limited to, shape area, dimensions of a rectangle bounding the shape, and the existence of a similar shape within a certain distance threshold from the shape. If the aforementioned shapes meet the above criteria, the shapes are considered to be successful matches.

The measurement module 108 then determines the distance between the first mark and the second mark created by the first laser 212/310 and the second laser 214/312 within the captured image, 706. In an illustrative embodiment, the distance between the first mark and the second mark created by the first laser 212/310 and the second laser 214/312 within the captured image is determined in terms of pixels.

Referring to FIG. 2A, the first laser 212 and the second laser 214 are spaced the distance D, for example, 16 mm, apart and are parallel with respect to one another. Therefore, the actual distance between the center of the first mark and the center of the second mark created by the first laser 212 and the second laser 214 within the captured image should be the distance D, for example, 16 mm. Referring to FIG. 7, using the distance D and the distance between the first mark and the second mark in pixels, the measurement module 108 determines a scaling factor for the captured image, 708. The measurement module 108 determines a distance in pixels of a measurement of the patient or object, illustrated as 710. Using the scaling factor, the measurement module 108 determines the actual dimensional measurements of the measurement of the patient or object captured in the image, 712.

One example of a measurement calculation of a dimensional measurement of an object is described herein. The distance D between the centers of the first laser 212 and the second laser 214 is 16 mm. The distance between the first mark and the second mark in pixels or pixel distance is determined to be 47 pixels. The scaling factor is D divided by the pixel distance, which is about 0.34 mm/pixels (16 mm/47 pixels=about 0.34 mm/pixels). Thus, the actual distance between two selected points in the captured image, for example, a distance between the patient's pupils, can be determined by determining the distance between the two selected points in pixels and multiplying the distance between the two selected points in pixels by the scaling factor. For example, if the distance between the two selected points in the captured image is 141 pixels the actual distance between the two selected points is 47.94 mm (141 pixels×0.34 mm/pixels=47.94 mm).

Figure 8:
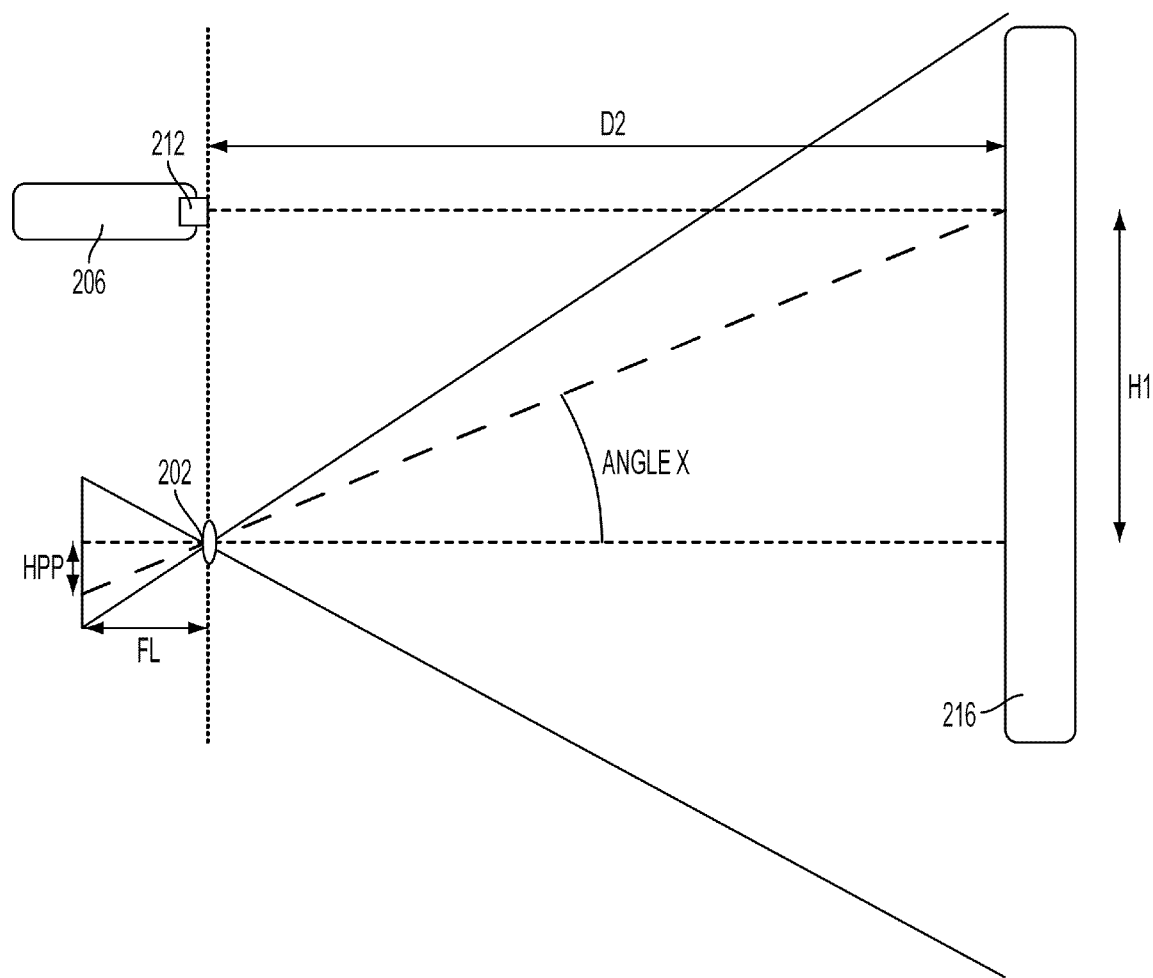
FIG. 8 illustrates a schematic for obtaining a distance measurement.
Figure 9:
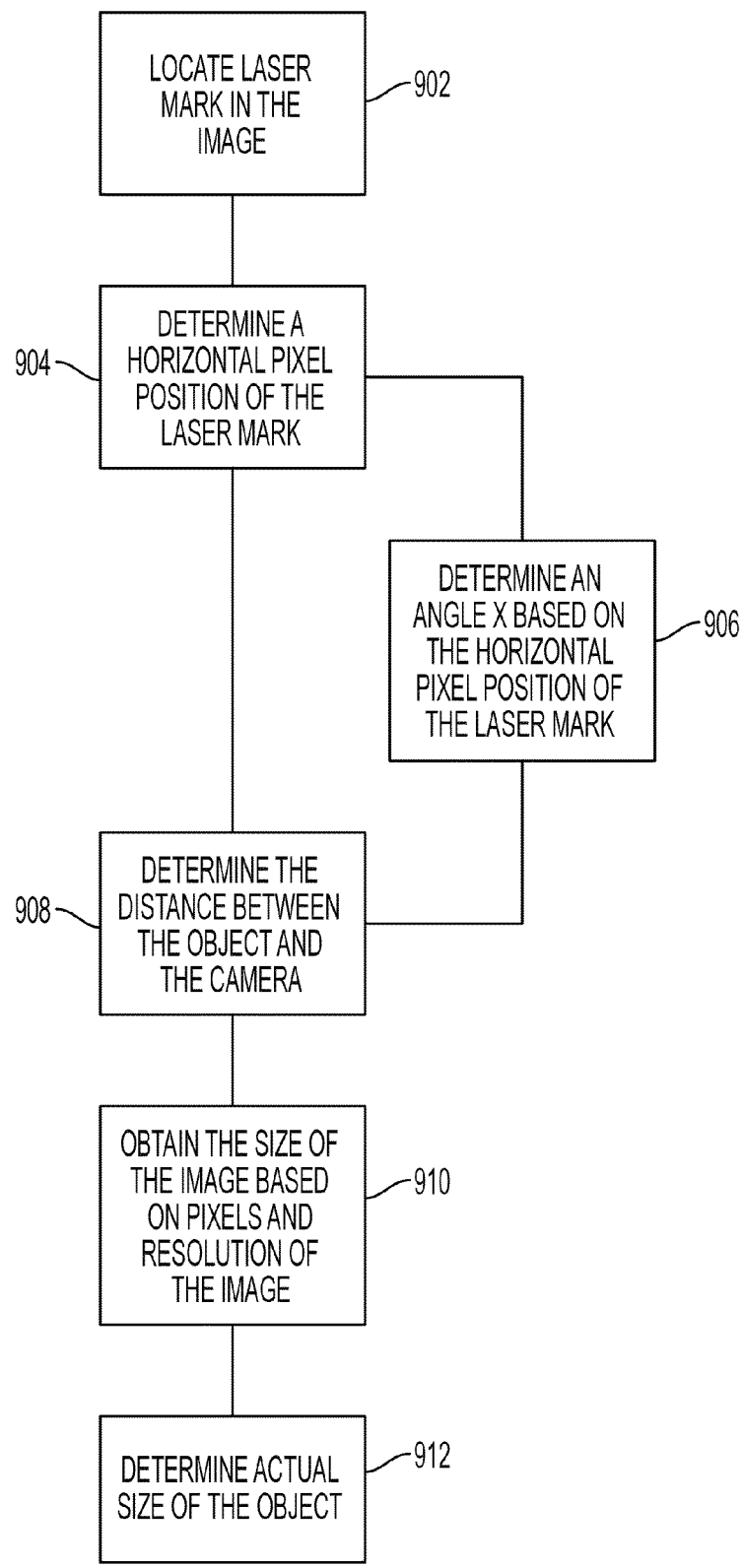
FIG. 9 illustrates a flow diagram of a method for obtaining a distance measurement.
Figure 10:
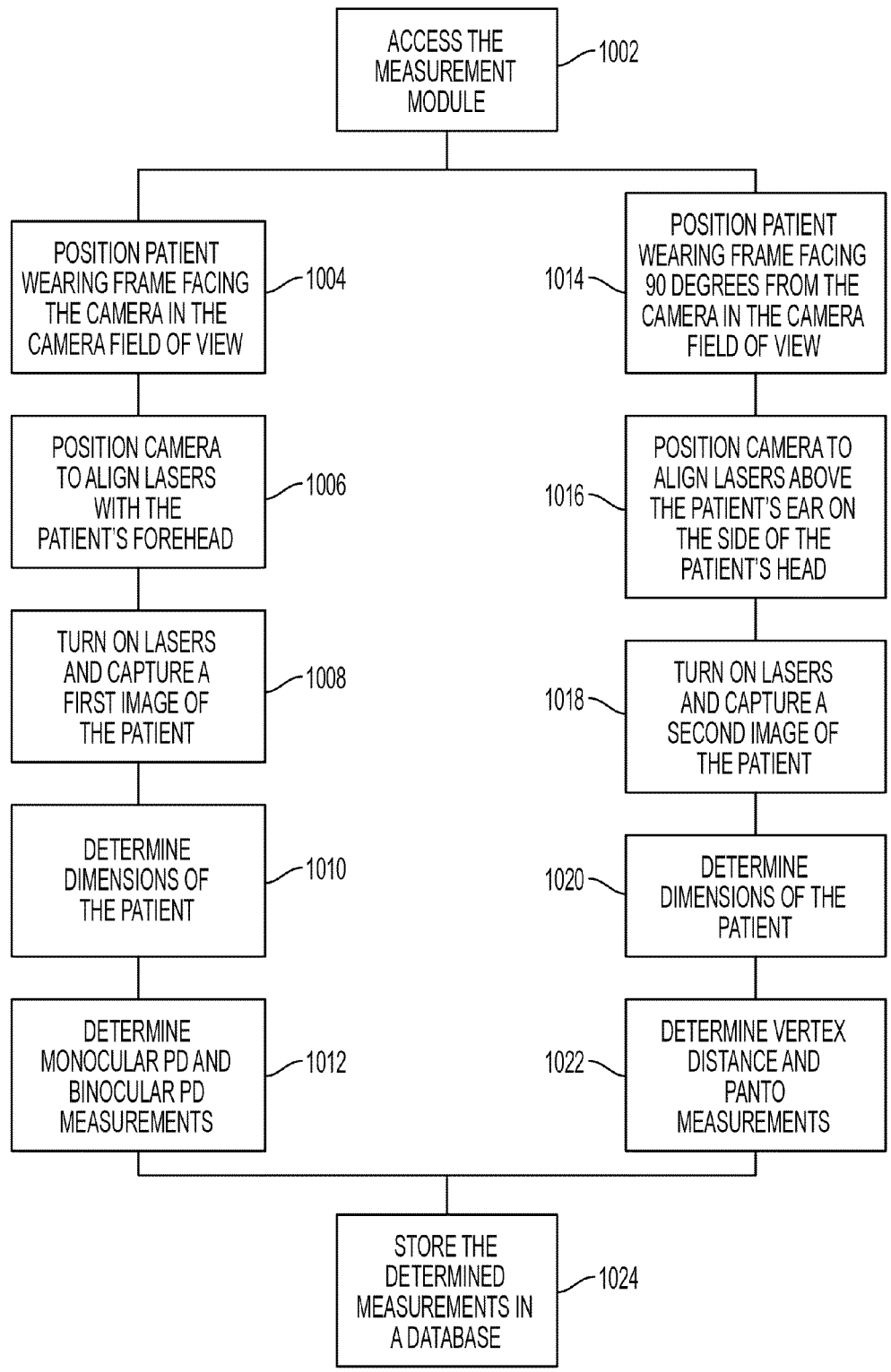
FIG. 10 illustrates a flow diagram of a method for obtaining position of wear measurements of a patient.

A method of obtaining a distance measurement according to an illustrative embodiment is described with reference to FIGS. 8 and 9. The measurement module 108 analyzes the captured image(s) and locates at least one of the first mark and the second mark created by the first and second lasers 212 and 214, respectively, within the captured image, 902. As illustrated in FIG. 8, only the first laser 212 is illustrated, however it should be appreciated by those skilled in the art that either one of the lasers 214, 310, or 312 may be used in the following method.

As illustrated in FIG. 8, the location of the first mark created by the first laser 212 within the captured image changes based on a distance D2 of the object 216 from the digital camera 202. As the distance D2 increases, an angle X decreases and the position of the first mark in the field of view of the digital camera 202 changes. The measurement module 108 may allow the user 104 to select the type of mobile client device 102 being used, for example the Apple® iPad®. The Apple® iPad® camera has a focal length (FL) of about 531 pixels. Referring to FIGS. 8 and 9, the measurement module 108 determines a horizontal pixel position (HPP) distance of the first mark relative to a center of the digital camera 202, illustrated as 904. The measurement module 108 may determine the angle X from the center line of the digital camera 202 to the position of the first mark based on the HPP and FL, illustrated as 906. Since the distance H1 between the first laser 212 and the digital camera 202 is known, the measurement module 108 determines the distance D2 between the object 216 and the digital camera 202, illustrated as 908. The distance D2 may be determined using the distance H1 and the angle X, or using the distance H1, the focal length FL, and the distance HPP.

One example of a distance calculation is described with reference to FIG. 8. The focal length FL of the digital camera 202 is 531 pixels. The distance H1 between the first laser 212 and the digital camera 202 is 30 mm. The HPP is determined by the measurement module 108 to be 40 pixels. The angle X=tan$^{-1}$(HPP/FL). The distance D2=H1/tan(angle X). Combining the formula for the angle X and the formula for the distance D2, D2=(H1×FL)/HPP. Using the formula for the angle X, the angle X is calculated to be about 4.31 degrees (tan$^{-1}$(40 pixels/531 pixels)=4.31 degrees). The distance D2 is calculated to be about 398.25 mm (30 mm/tan(4.31)=398.25 mm). Alternatively, using the combined formula, D2 is calculated to be about 398.25 mm ((30 mm×531 pixels)/40 pixels=398.25 mm).

In an other illustrative embodiment, the laser measuring device 206/302 may include a light receiver. The laser measuring device 206/302 may measure the time required for at least one of a first laser beam and a second laser beam created by the first laser 212/310 and the second laser 214/312, respectively, to travel to a patient or an object, reflect off of the patient or object, and travel back to the light receiver. By measuring the time for the at least one of a first laser beam and a second laser bean created by the first laser 212/310 and the second laser 214/312 to be received by the light receiver, the distance (for example, D2) between the digital camera 202 and the patient or object can be determined.

Once the distance D2 is determined, the measurement module 108 can determine the actual size of the patient or object based on the captured image. Referring back to FIG. 9, the mobile client device 102 obtains the size of the image based on the number of pixels and the resolution of the digital camera 202, illustrated as 910. Based on the size of the image and the distance D2, the measurement module 108 can determine the actual size of the patient or object, illustrated as 912.

Referring to FIGS. 1-4 and 10, the mobile client device 102 with the laser measurement device 206/302 attached, as described above, may be used to obtain, for example, monocular pupillary distance (PD), binocular PD measurements, vertex distance, and pantoscopic tilt (panto) measurements of a patient from one or more images of the patient wearing a selected frame. In general, the ECP fits the frame to the patient prior to taking the one or more images of the patient.

As illustrated, the user 104 accesses the measurement module 108 via the mobile client device 102, illustrated as 1002. In order to obtain or calculate the monocular PD, which is the distance from each of the patient's pupils, using light reflected from the cornea, to the center of the patient's nose where the center of the frame bridge rests, and the binocular PD, which is the distance between the patient's pupils, the patient should be facing the digital camera 202 or mobile client device 102. The user 104 then positions the patient wearing the selected frame, with the patient facing the digital camera 202 or mobile client device 102 in the field of view of the digital camera 202, illustrated as 1004.

The user 104 also positions the digital camera 202 or mobile client device 102 to cause the first laser 212/310 and the second laser 214/312 to align with the patient's forehead or other substantially flat portion of the patient's head, 1006. The mobile client device 102 controls the first laser 212/310 and the second laser 214/312 so that the first laser 212/310 and the second laser 214/312 are only on during a very brief time when the image is captured. Since the first laser 212/310 and the second laser 214/312 are low power and are only on briefly, the first laser 212/310 and the second laser 214/312 should be minimally noticeable to the patient. This also means there should be no danger to the eyes of the patient when the first laser 212/310 and the second laser 214/312 are activated.

With the digital camera 202 or mobile client device 102 positioned the user 104 simultaneously activates the first laser 212/310 and the second laser 214/312 and captures a first image of the patient, for example, by pressing a button on the mobile client device 102, illustrated as 1008. Once the mobile client device 102 captures the first image of the patient, the measurement module 108 analyzes the first image, for example using facial recognition and 3-D rendering technology, and determines the size and dimensions of the patient, for example, as described above with reference to FIGS. 7-9, illustrated as 1010. The measurement module 108 then analyzes the image and determines or calculates the monocular PD and the binocular PD measurements of the patient, 1012.

In an example, using the method described above with reference to FIG. 7, the distance D between the centers of the first laser and the second laser is 16 mm, and the measurement module 108 determines the distance between the first mark and the second mark in the first image in pixels or a pixel distance to be 47 pixels. The scaling factor is D divided by the pixel distance, which is about 0.34 mm/pixels (16 mm/47 pixels=about 0.34 mm/pixels). The monocular PD is determined by determining the distance from each of the patient's pupils to the center of the patient's nose. In this example, the measurement module 108 determines the pixel distance from the center of the patient's right pupil to the center of the patient's nose in the first image to be 70 pixels, and the pixel distance from the center of the patient's left pupil to the center of the patient's nose in the first image to be 70 pixels. The measurement module 108 determines the patient's monocular PD by multiplying the pixel distances by the scaling factor. The patient's monocular PD for the right eye is 23.8 mm (70 pixels×0.34 mm/pixels=23.8 mm), and the patient's monocular PD for the left eye is 23.8 mm (70 pixels×0.34 mm/pixels=23.8 mm).

The binocular PD is determined by determining the distance between the centers of each of the patient's pupils. In this example, the measurement module 108 determines the pixel distance between the centers of each of the patient's pupils in the first image to be 140 pixels. The measurement module 108 determines the patient's binocular PD by multiplying the pixel distance by the scaling factor. The patient's binocular PD is 47.6 mm (140 pixels×0.34 mm/pixels=47.6 mm)

In order to obtain or calculate the vertex distance, which is the distance between the back surface of a lens and the front of the cornea of the patinet, and the pantoscopic tilt, which is the angle between the plane of the lens and frame front and the frontal plane of the face, the patient should be facing about ninety degrees away from the digital camera 202 or mobile client device 102. The user 104 positions the patient wearing the selected frame, with the patient facing about ninety degrees away from the digital camera 202 or mobile client device 102, in the field of view of the digital camera 202, illustrated as 1014.

The user 104 also positions the digital camera 202 or mobile client device 102 to cause the first laser 212/310 and the second laser 214/312 to align with the side of the patient's head above the patient's ear or other substantially flat portion of the patient's head, 1016. The user 104 simultaneously activates the first laser 212/310 and the second laser 214/312 and captures a second image of the patient, 1018. The measurement module 108 analyzes the second image, for example, using facial recognition and 3-D rendering technology, and determines the size and dimensions of the patient, for example, as described above with reference to FIGS. 7-9, illustrated as 1020. The measurement module 108 then analyzes the image and determines or calculates the vertex distance and pantoscopic tilt measurements of the patient wearing the selected frames 1022.

In an example, using the method described above with reference to FIG. 7, the distance D between the centers of the first laser and the second laser is 16 mm, and the measurement module 108 determines the distance between the first mark and the second mark in the second image in pixels or a pixel distance to be 47 pixels. The scaling factor is D divided by the pixel distance, which is about 0.34 mm/pixels (16 mm/47 pixels=about 0.34 mm/pixels). The vertex distance is determined by determining the distance between a back surface of a lens and a front of a cornea of the patient. In this example, the measurement module 108 determines the pixel distance from the back surface of the lens to the front of the cornea of the patient's eye in the second image to be 15 pixels. The measurement module 108 determines the vertex distance by multiplying the pixel distance by the scaling factor. The vertex distance is 5.1 mm (15 pixels×0.34 mm/pixels=5.1 mm).

The pantoscopic tilt is determined by determining an angle between a plane of the lens and frame front and a frontal plane of the patient's face. In this example, the frontal plane of the patient's face is vertical, and the plane of the lens and frame front is tilted, for example, creating a hypotenuse (Hyp.) of a right triangle with a height of the right triangle or an adjacent side (Adj.) of the right triangle being the frontal plane of the patient's face. A horizontal distance from the frontal plane of the patient's face to the plane of the lens and frame front creates an opposite side of the right triangle. The lengths of the hypotenuse and the adjacent side are the respective distances from the opposite side of the right triangle to a point where the frontal plane of the patient's face and the plane of the lens and frame front intersect. The measurement module 108 can determine the length in pixels of each of the sides of the right triangle. In this example, the measurement module 108 determines the pixel length of the adjacent side to be 12 pixels, and the pixel length of the hypotenuse of the right triangle to be 12.1 pixels. The measurement module 108 then determines the pantoscopic tilt by calculating the inverse cosine of the pixel length of the adjacent side divided by the pixel length of the hypotenuse (pantoscopic tilt=$\cos^{-1}$(Adj./Hyp.)). The pantoscopic tilt is 7.3 degrees ($\cos^{-1}$(12/12.1)=7.3 degrees). It should be appreciated that the method of calculating the pantoscopic tilt measurement described above is one of many ways to calculate the pantoscopic tilt, and that the pantoscopic tilt measurement may be calculated using various other geometry type calculations known in the art.

The measurement module 108 may store the monocular PD, binocular PD, vertex distance, pantoscopic tilt, and other measurements in the one or more databases 110, illustrated as 1024. In an illustrative embodiment, the measurements are stored in association with the patient's personal information allowing the patient's specific measurements to be retrieved by the user 104 via the mobile client device 102 if desired.

Figure 11:
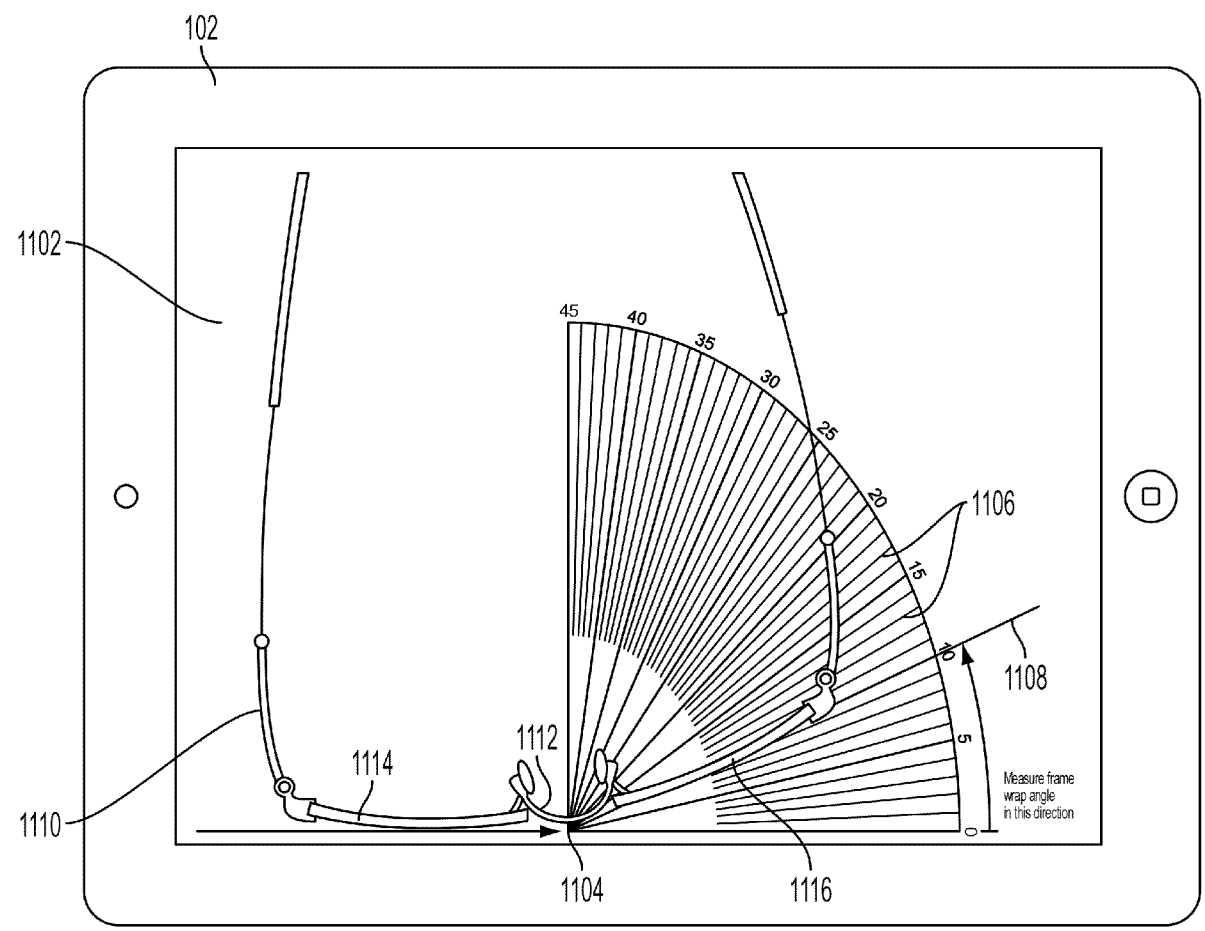
FIG. 11 illustrates an embodiment of an interactive frame wrap measurement tool displayed on the mobile client device.

In an illustrative embodiment, the mobile client device 102 may also be used to determine a frame wrap measurement of the selected frames. A frame wrap measurement tool on the mobile client device 102 according to an illustrative embodiment is described with reference to FIG. 11. As illustrated in FIG. 11, the measurement module 108 also includes a frame wrap measurement tool 1102 that may be displayed on the mobile client device 102. The frame wrap tool 1102 includes a center point 1104 and a number of angular measurement lines 1106 extending from the center point 1104 at varying angles, for example, beginning at a zero degree angle and ending at a forty-five degree angle with angular measurement lines 1106 for each incremental degree therebetween.

The frame wrap measurement tool 1102 also includes an interactive measurement line 1108 having a pivot point at the center point 1104. The interactive measurement line 1108 extends from the center point 1104 and is movable by the user 104 to align with each of the various angular measurement lines 1106. In an illustrative embodiment, the mobile client device 102 includes a touch-screen display and the user 104 moves or positions the interactive measurement line 1108 by, for example, stylus or touch, and pivoting the interactive measurement line 1108 to align with a desired angular measurement line 1106. In another illustrative embodiment, the user 104 moves or positions the interactive measurement line 1108 by clicking on and pivoting the interactive measurement line 1108 using a computer mouse or other computer device.

To measure the frame wrap measurement of a selected frame 1110, the user 104 accesses the frame wrap measurement tool 1102 of the measurement module 108. The frame wrap measurement tool 1102 is then displayed on the mobile client device 102, for example, on the touch-screen display of the mobile client device 102. The user 104 places the selected frame 1110 on the touch-screen display of the mobile client device 102 and aligns the center of a bridge 1112 of the selected frame 1110 with the center point 1104 of the frame wrap measurement tool 1102. The user 104 also aligns a first lens 1114 of the selected frame 1110 parallel to the zero degree angular measurement line. A second lens 1116 of the selected frame 1110 will be aligned parallel to one of the various angular measurement lines 1106 of the frame wrap measurement tool 1102. The user 104 then pivots the interactive measurement line 1108 to align parallel to the second lens 1116 of the selected frame 1110. The interactive measurement line 1108 will align with one of the angular measurement lines 1106 indicating a frame wrap angle or frame wrap measurement of the selected frame 1110.

The measurement module 108 may store the frame wrap measurement in the one or more databases 110. Similarly, the frame wrap measurement may be stored in association with the patient's personal information allowing the frame wrap measurement of the frame selected by the patient to be retrieved by the user 104 via the mobile client device 102 if desired.

In an illustrative embodiment, the monocular PD, binocular PD, vertex distance, pantoscopic tilt, and frame wrap measurements may then be sent to the one or more ophthalmic laboratories 112 along with a patient's frame and lens order via the mobile client device 102. The one or more ophthalmic laboratories 112 may use the measurements to produce customized lenses for the patient. For example, the one or more ophthalmic laboratories 112 may use the measurements and the patients prescription to determine a compensated prescription for the patient's lenses based on the selected frames and the patient's position of wear measurements.

Figure 12:
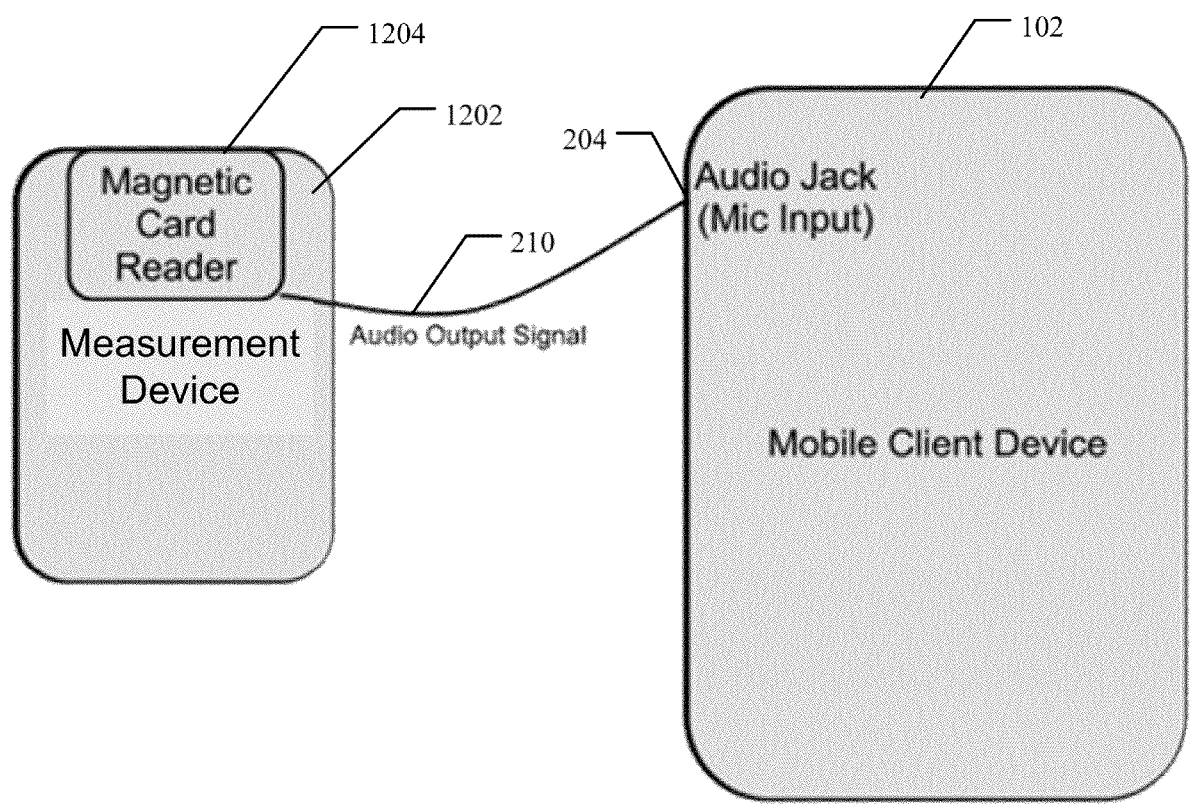
FIG. 12 illustrates a functional block diagram of an embodiment of a laser measurement device including a magnetic card reader.

Another embodiment of a laser measurement device including a magnetic card reader is described with reference to FIG. 12. As illustrated in FIG. 12, a laser measurement device 1202 includes a magnetic card reader or magnetic card reader head 1204. Similar to the laser measurement devices described above, the laser measurement device 1202 including the magnetic card reader 1204 are electrically connected to the mobile client device 102 via the audio port 204 by wiring 210.

The magnetic card reader 1204 is a compact, self-contained module configured to read a magnetic pattern or data on a magnetic strip of a card, such as a credit card, debit card, or other card with a magnetic strip, and convert the magnetic pattern or data to an electrical signal. In an illustrative embodiment, when a card is swiped across a card slot (for example, card slot 1324 described below) in the laser measurement device 1202, the magnetic card reader 1204 converts the magnetic pattern on the card into the electrical signal. The resulting electrical signal produced is within the range and level of an audio signal, and the magnetic card reader 1204 outputs the electrical signal on two terminals. The electrical signal is then input to the audio port 204 of the mobile client device 102 via the wiring 210.

In an illustrative embodiment, the mobile client device 102 includes or accesses a credit card reader module, which may be a software application executable by a processor in the mobile client device 102, stored in an internal storage device of the mobile client device 102 or in the computing infrastructure 106. The credit card reader module converts the electrical signal obtained from the magnetic strip to digital data which represents the information that is stored on the card using one or more algorithms, as known in the art.

The card reader module also incorporates one or more security measures, for example, encryption of the digital data, to ensure the digital data is available and accessible only for authorized purposes. The digital data may then be communicated or transferred to a credit card processing service, for example, via the computing infrastructure 106, for verifying the information, processing a transaction, and transferring payment.

Figure 13:
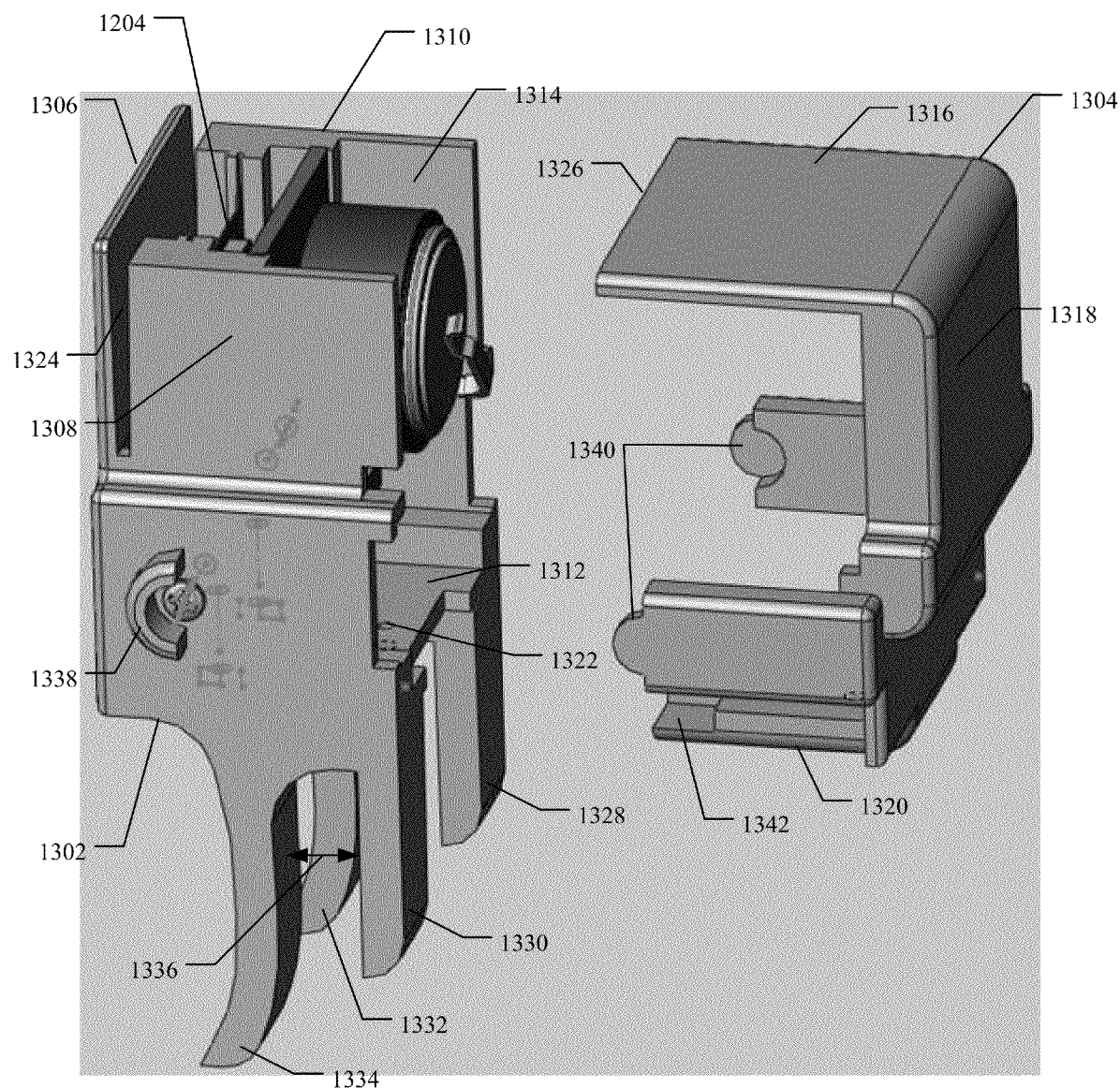
FIG. 13 illustrates an exploded perspective view of the laser measurement device of FIG. 12.

Similar to the laser measurement devices described above, the laser measurement device 1202 including the magnetic card reader 1204 may include a housing and lasers. An illustrative embodiment of the laser measurement device 1202 is described with reference to FIGS. 13-15. As illustrated in FIG. 13, the laser measurement device 1202 includes a housing 1302 including a cover portion 1304. The housing 1302 and the cover portion 1304 are adapted to house internal components of the laser measurement device 1202 including the magnetic card reader 1204. The cover portion 1304 may be removable to provide access to the internal components.

In an illustrative embodiment, the housing 1302 includes a first side or front face 1306, a second side 1308 perpendicular to the first side 1306, a third side 1310 opposite the second side 1308 and perpendicular to the first side 1306, and a fourth side or bottom 1312 extending from and perpendicular to the first side 1306 and extending between the second side 1308 and the third side 1310. The first side 1306, second side 1308, third side 1310, and fourth side 1312 form an internal compartment 1314 in which the internal components may be disposed. The cover portion 1304 includes a fifth side or top 1316 and a sixth side or rear face 1318 extending from and perpendicular to the fifth side 1316. The cover portion 1304 may be disposed or slid onto the housing 1302. The fifth side 1316 and the sixth side 1318 are arranged to enclose the internal compartment 1314 formed by the first side 1306, second side 1308, third side 1310, and fourth side 1312 of the housing 1302. In this illustrative embodiment, the fifth side 1316 extends from the second side 1308 to the third side 1310 opposite the fourth side 1312, and the sixth side 1318 extends from the second side 1308 to the third side 1310 and from the fourth side 1312 to the fifth side 1316 opposite the first side 1306.

In an illustrative embodiment, the cover portion 1304 may also include a fastening portion 1320 extending from the sixth side 1318 and opposite the fifth side 1316. The fastening portion 1320 abuts an external surface of the fourth side 1312 of the housing 1302 when the cover portion 1304 is installed on the housing 1302. The fourth side 1312 of the housing 1302 may include a fastener aperture 1322 and the fastening portion 1320 may include a corresponding fastener aperture. A fastener, for example, a screw, bolt, rivet, nail and other fastener of the type, may be disposed within the fastener aperture 1322 and the corresponding fastener aperture to attach or secure the cover portion 1304 to the housing 1302.

In this illustrative embodiment, the housing 1302 includes a card slot 1324 through which a card, for example, a card with a magnetic strip, such as a credit card, may be slid through. As illustrated in FIG. 13, the card slot 1324 is located between the first side 1306 and the second side 1308, third side 1310, and an end 1326 of the fifth side 1316 opposite the sixth side 1318. While the card slot 1324 is described and illustrated as being located between the first side 1306 and the second side 1308, third side 1310, and an end 1326 of the fifth side 1316 opposite the sixth side 1318, it should be appreciated that the card slot 1324 may be positioned in any number of different locations in, on, or around the housing 1302 and/or the cover portion 1304.

The magnetic card reader 1204 is disposed within the housing 1302 in proximity to the card slot 1324 to allow the magnetic card reader 1204 to read a magnetic pattern or data on a magnetic strip of a card, such as a credit card, debit card, or other card with a magnetic strip, when the card is swiped through the card slot 1324. The magnetic card reader 1204 may convert the magnetic pattern or data to an electrical signal, as described above with reference to FIG. 12.

Similar to the embodiments of the laser measurement devices described above, the housing 1302 includes a first support 1328 and a second support 1330 attached to or monolithically formed with the housing 1302 and protruding or extending vertically downward from the fourth side 1312 or perpendicular to the fourth side 1312. As illustrated, the first support 1328 and the second support 1330 are aligned with one another, horizontally along the fourth side 1312 from the second side 1308 to the third side 1310. Similarly, a third support 1332 and a fourth support 1334 are attached to or monolithically formed with the housing 1302 and protrude or extend vertically downward from the fourth side 1312 or perpendicular to the fourth side 1312. The third support 1332 and a fourth support 1334 are aligned with one another, horizontally along the fourth side 1312 from the second side 1308 to the third side 1310. The supports 1328, 1330, 1332, and 1334 form one or more notches 1336 between the first support 1328 and the third support 1332 and between the second support 1330 and the fourth support 1334. The one or more notches 1336 allow for the housing 1302 or the laser measurement device 1202 to be placed on the mobile client device 102, for example, as described above with reference to FIG. 4.

Figure 14:
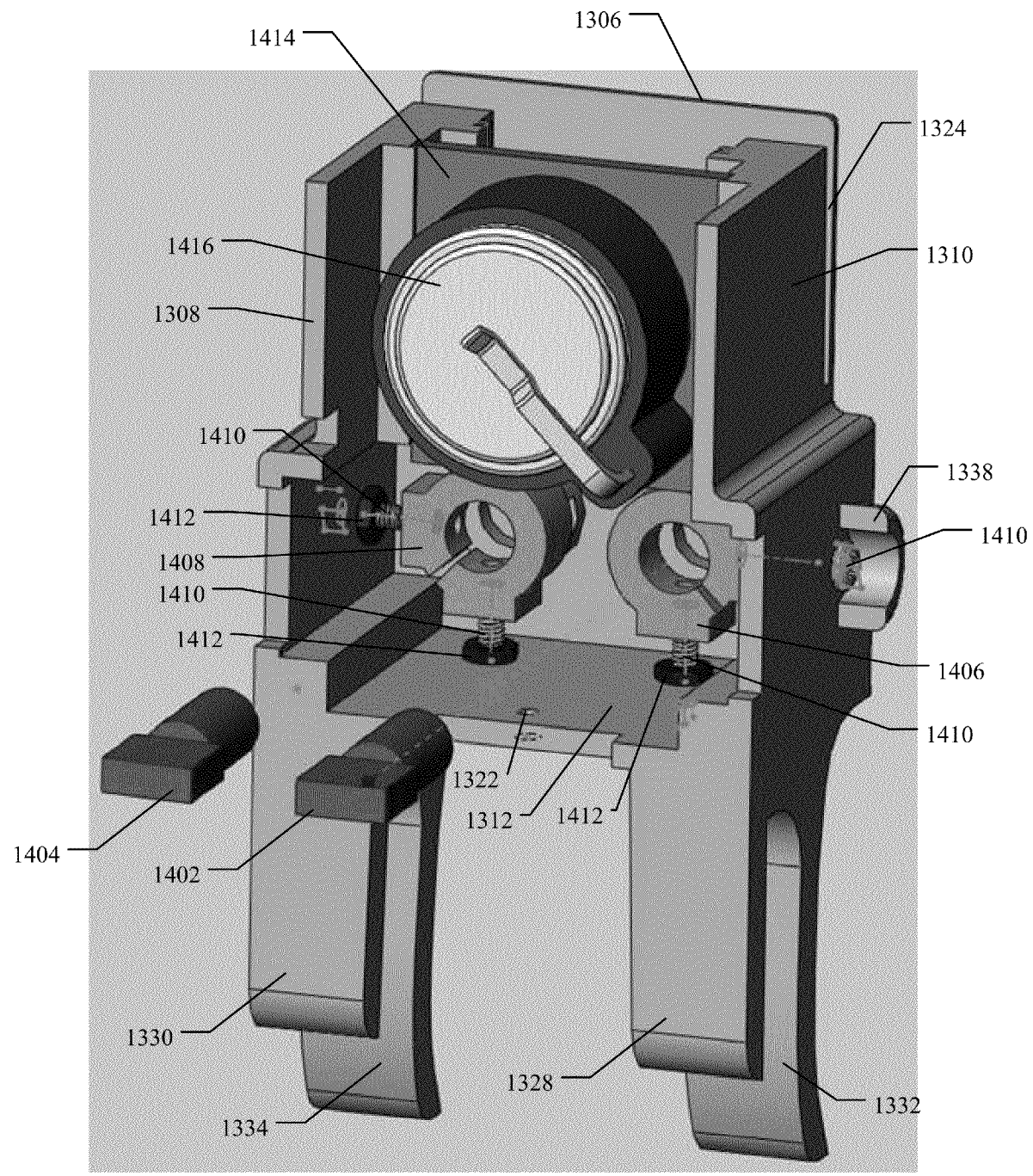
FIG. 14 illustrates a perspective view illustrating internal components of the laser measurement device of FIG. 13.

Referring to FIG. 14, a first laser 1402 and a second laser 1404, which may be the same as the first and second lasers 310, 212 and 312, 214, respectively, are positioned within the internal compartment 1314 of the housing 1302. As illustrated, the first laser 1402 and the second laser 1404 are positioned next to each other, horizontally along the first side 1306 between the second side 1308 and the third side 1310, and are in parallel alignment with one another. The first laser 1402 and the second laser 1404 may be aligned to transmit through a first aperture and a second aperture (such as the first aperture 1802 and the second aperture 1804 illustrated FIG. 18), respectively, in the first side 1306 of the housing 1302.

As illustrated in FIG. 14, the first laser 1402 and the second laser 1404 are disposed or mounted within a first connector 1406 and a second connector 1408, respectively, disposed within the internal compartment 1314 of the housing 1302. The first and second connectors 1404 and 1406, respectively, are held in place within the housing 1302 by fasteners 1410 extending through the corresponding second side 1308, third side 1310, and fourth side 1312 of the housing 1302 and are threaded into the corresponding first and second connectors 1404 and 1406, respectively. In this illustrative embodiment, the fasteners 1410 are threaded screws or bolts and include corresponding threaded nuts 1412. The nuts 1412 are threaded onto the corresponding fasteners 1410 and positioned proximal to the corresponding second side 1308, third side 1310, and fourth side 1312 of the housing 1302. The first and second connectors 1404 and 1406, respectively, can be used to align or calibrate the position of the first and second lasers 1402 and 1404, respectively, by rotating the corresponding fasteners 1410. In one illustrative embodiment, the first and second lasers 1402 and 1404, respectively, are calibrated to transmit laser marks that are in parallel alignment and about sixteen (16) millimeters apart at a distance of about two (2) meters from the location of the first and second lasers 1402 and 1404, respectively.

In an illustrative embodiment referring to FIGS. 13 and 14, the housing 1302 includes at least one protrusion 1338 extending from an external surface of each of the second side 1308 and the third side 1310. As illustrated, the protrusions 1338 are positioned or located proximal to the fasteners 1410. The cover portion 1304 may include cover protrusions 1340 extending perpendicularly from the sixth side 1318 between the fastening portion 1320 and the fifth side 1316. The cover protrusions 1340 are positioned or located to mate with the protrusions 1338 and enclose or cover the fasteners 1410 that extend through the second side 1308 and the third side 1310, respectively. The fastening portion 1320 of the cover portion 1304 may also include one or more recesses or notches 1342 adapted to enclose or cover the fasteners 1410 that extend through the fourth side 1312. The protrusions 1338 and the corresponding cover protrusions 1340 and the recesses or notches 1342 in the fastening portion 1320 protect the fasteners 1410 from being rotated when the first and second lasers 1402 and 1404, respectively, are not being calibrated to reduce the risk that or prevent the first and second lasers 1402 and 1404, respectively, from being accidentally repositioned or taken out of alignment.

In an illustrative embodiment, the laser measurement device 1202 includes control circuitry 1414, for example, a printed circuit board, disposed within the internal compartment 1314 of the housing 1302, and a power source 1416 disposed within the internal compartment 1314 of the housing 1302. The control circuitry 1414 is electrically connected to the first and second lasers 1402 and 1404, respectively, and the power source 1416 is electrically connected to the control circuitry 1414 and the first and second lasers 1402 and 1404, respectively. The control circuitry 1414 and the power source may be the same control circuitry and power source as described above with reference to FIG. 5, for example, to activate the first and second lasers 1402 and 1404, respectively by receiving an audio signal from the mobile client device 102 via the audio port 204.

Figure 15:
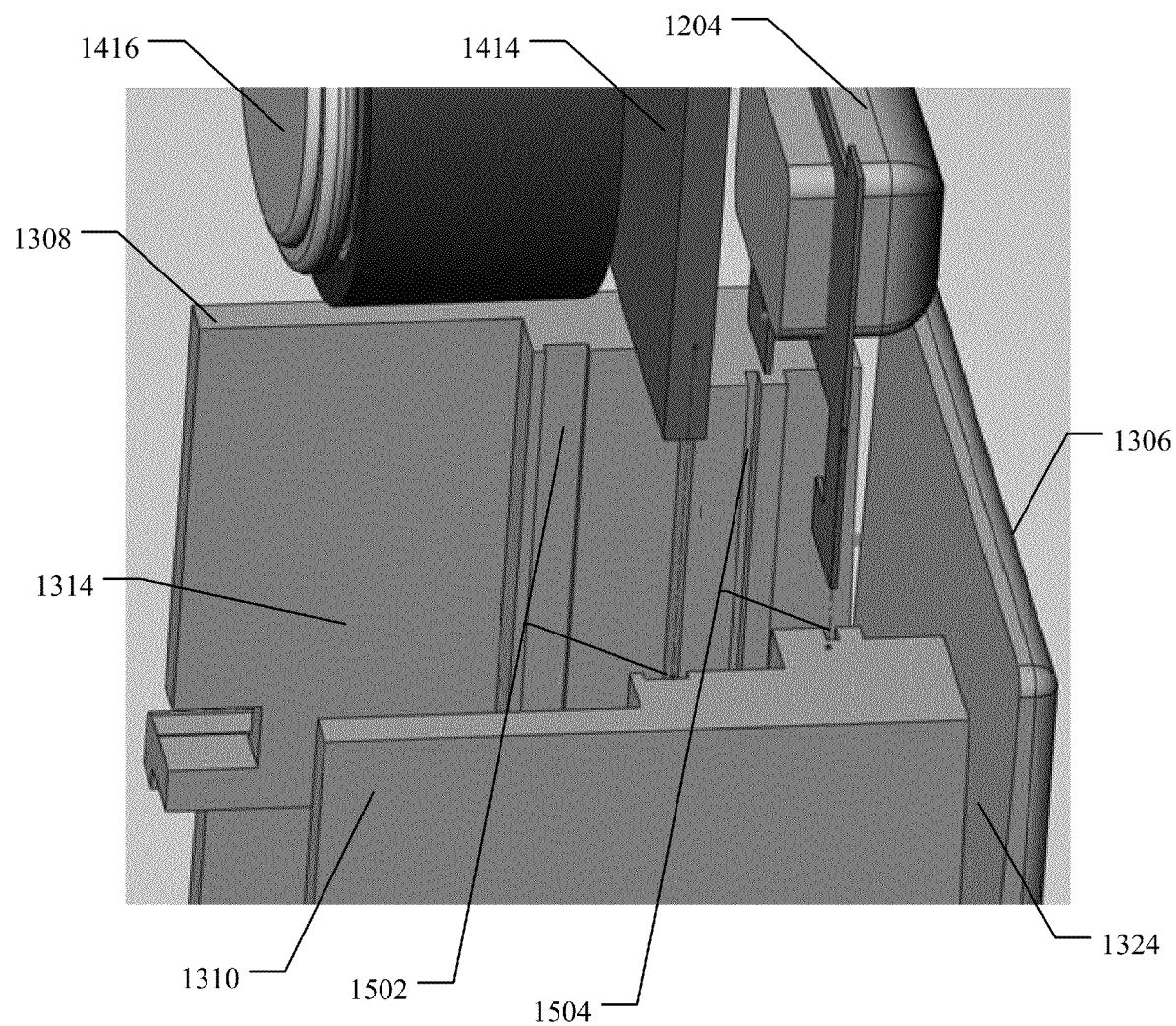
FIG. 15 illustrates an exploded perspective view of a power source, printed circuit board, and magnetic reader of the laser measurement device of FIGS. 13 and 14.

In an illustrative embodiment, referring to FIG. 15, the housing 1302 includes corresponding first slots or notches 1502 in or on internal surfaces of the corresponding second side 1308 and the third side 1310. The first slots 1502 are adapted to receive and retain the control circuitry 1414 within the internal compartment 1314. Similarly, the housing 1302 includes corresponding second slots or notches 1504 in or on the internal surfaces of the corresponding second side 1308 and the third side 1310. The second slots 1504 are adapted to receive and retain the magnetic card reader 1204 within the internal compartment 1314 and in proximity to the card slot 1324.

Figure 16:
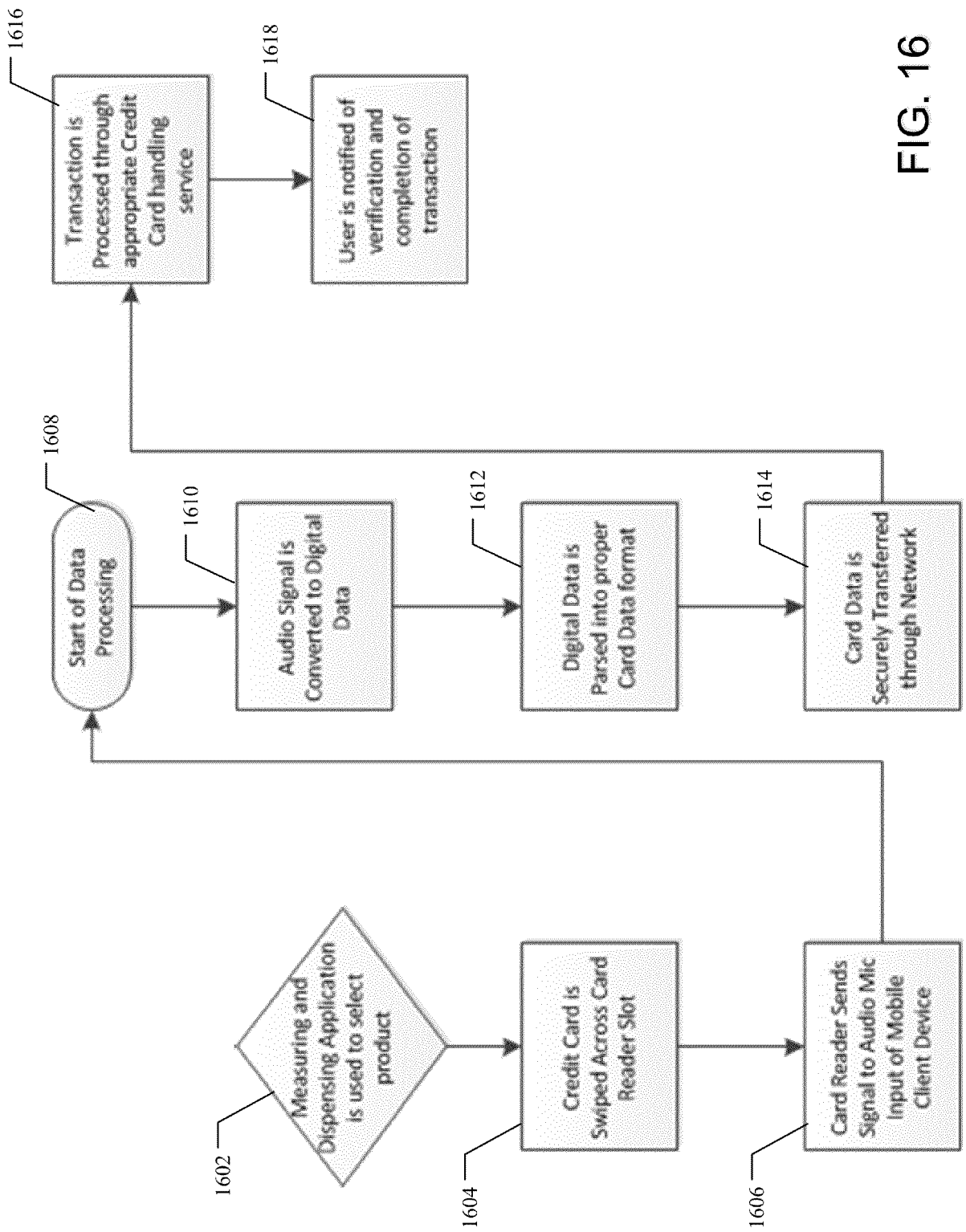
FIG. 16 illustrates a flow diagram of a method of using the mobile client device and the laser measurement device of FIGS. 12-15.
Figure 17:
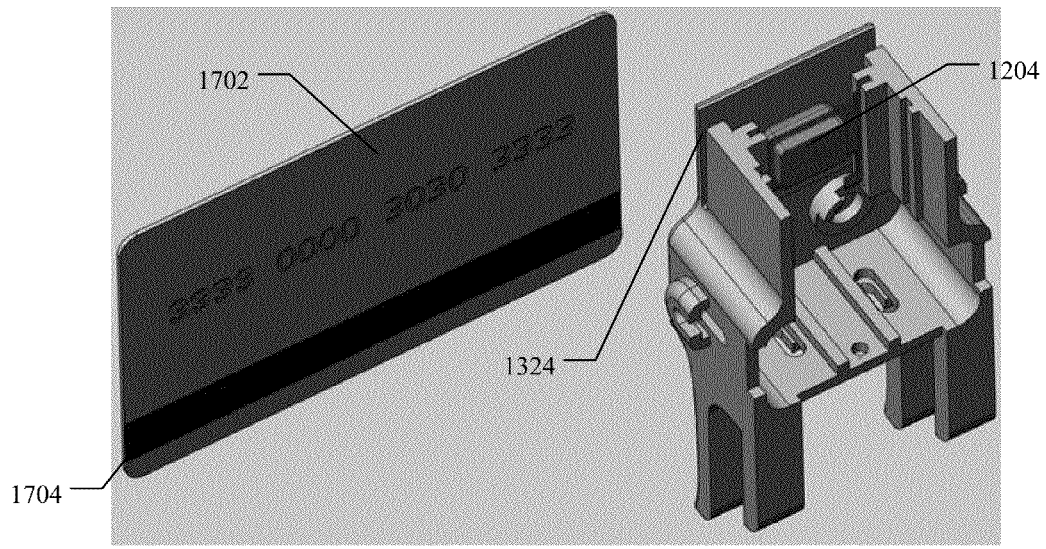
FIG. 17 illustrates a first perspective view of the magnetic reader of the laser measurement device of FIGS. 13-15.
Figure 18:
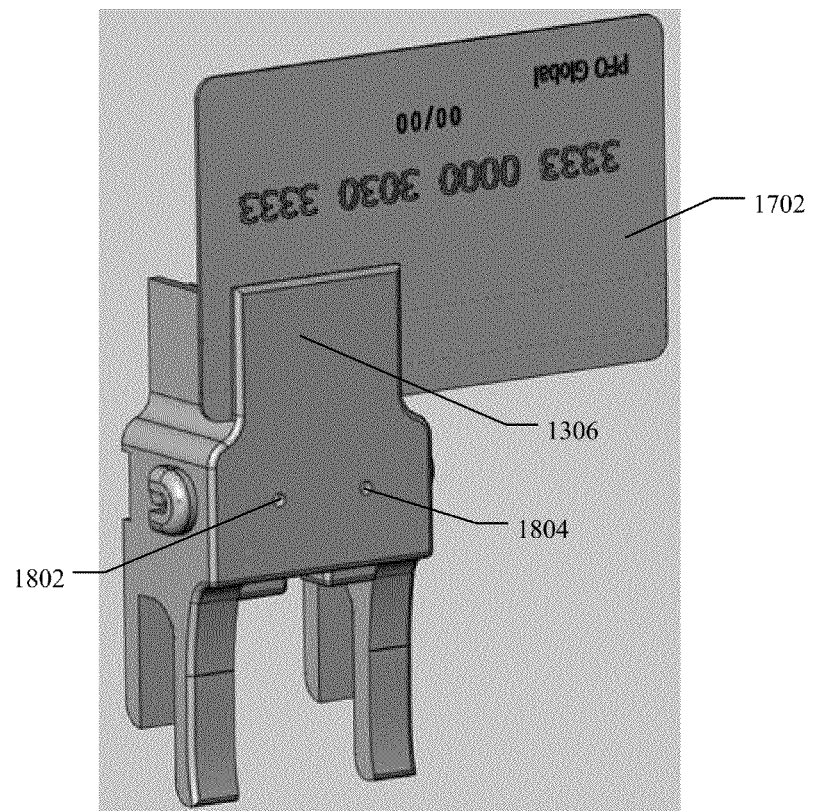
FIG. 18 illustrates a second perspective view of the magnetic reader of the laser measurement device of FIGS. 13-15 and 17.

A method of using the magnetic card reader and the mobile client device according to an illustrative embodiment is described with reference to FIGS. 16-18. A user or patient may select 1603 a product, for example, a frame and lenses, using the mobile client device 102. In an illustrative embodiment, the lenses selected may be prescription lenses determined by an eye care professional. The laser measurement device 1202 may also be used to determine the monocular PD, binocular PD, vertex distance, pantoscopic tilt, and frame wrap measurements of the frame selected by the user. The patient's order or product selection may be sent to the one or more ophthalmic laboratories 112 along with the patient's measurements via the mobile client device 102 upon completion or pending a transaction, for example, a payment transaction.

The mobile client device 102 and the magnetic card reader 1204 of the laser measurement device 1202 may be used to complete the payment transaction. In an illustrative embodiment, a user's credit card is swiped 1604 through the card slot 1324. Referring to FIGS. 17 and 18, a credit card 1702 having magnetic strip 1704 is illustrated as being swiped through the card slot 1324. In FIGS. 17 and 18, the majority of the internal component of the laser measurement device 1202 are not illustrated in order to illustrate the relationship of the magnetic card reader 1204 and the card slot 1324.

Referring back to FIG. 16, upon the user's credit card being swiped, the magnetic card reader 1204 converts the magnetic pattern on the user's credit card into the electrical signal and sends or inputs 1606 the electrical signal to the audio port 204 of the mobile client device 102 via the wiring 210. The mobile client device 102 receives the electrical signal and begins processing 1608 the electrical signal. To process the electrical signal, the mobile client device 102 converts 1610 the signal to digital data which represents the information that is stored on the card. The mobile client device 102 parses 1612 the digital data into the proper format for the user's credit card. As described above, the mobile client device 102 may access the credit card reader module to convert the signal and parse the data.

The digital data may then be communicated or transferred 1614 securely, for example, via encryption, to a credit card processing service through a network, for example, via the computing infrastructure 106. The credit card processing service verifies and processes 1616 the transaction. The user is notified 1618 of the verification and completion of the transaction by the credit card processing service, for example, via the mobile client device 102.

It should be appreciated by those skilled in the art that the housing 1302 may be assembled together from multiple separate pieces or, as illustrated, monolithically formed as a single piece. Similarly, the cover portion 1304 may be assembled together from multiple separate pieces or, as illustrated, monolithically formed as a single piece. Further, while the internal components of the laser measurement device 1202 are described and illustrated in certain arrangements, it should be appreciated by those skilled in the art that the internal components may be arranged differently within the housing 1302 of the laser measurement device 1202.

Although the magnetic card reader is described for reading credit card information, the magnetic card reader can be used to read other information on a magnetic strip, for example, personal information, medical information, prescription information, and other information of the type. Further, although the card reader is described as a magnetic card reader, the card reader could be an integrated technology for reading other technologies, for example, a bar code, Radio-frequency identification (RFID), or other wireless readers or the like.

In an illustrative embodiment, the mobile client device 102 may be in communication with a practice management interface (PMI) or practice management system/software (PMS), for example, Compulink by Compulink Business Systems, Inc. of Westlake Village, Calif., MaximEyes by First Insight-Optometry of Hillsboro, Oreg., OfficeMate by Eyefinity, Inc. of Rancho Cordova, Calif., or AcuityLogic by Eyefinity, Inc. of Rancho Cordova, Calif., and other PMIs/PMSs of the type. In an illustrative embodiment, the mobile client device 102 is integrated into the PMI. In this illustrative embodiment, the mobile client device 102 is configured to collect data, receive data, and transmit data within the PMI, for example, patient information, frame information, lens information, and the measurements obtained/calculated as described above.

In an illustrative embodiment, the mobile client device 102 may be continually or periodically connected to the computing infrastructure 106 or separate/disconnected from the computing infrastructure 106. The network may be a local area network or a wide area network and may be a private or public network of any size or scope. In an illustrative embodiment, the network is the Internet. Although the module 108 is described as being in the computing infrastructure 106, the module 108 may be included within the mobile client device 102 or different functions of the module 108 may be distributed between the computing infrastructure 106 and mobile client device 102.

In an illustrative embodiment, the mobile client device 102 may allow the user 104 to interact with the mobile client device 102, receive, and/or collect data from the user 104 through the use of a client/user interface or graphical user interface, for example, an interface installed on the mobile client device 102, an application, and/or a remotely accessible interface. The user interface may include visual, audio, graphics, charts, and other features of the type. The user interface may include one or more menus incorporating a number of specific questions, prompts, selections/buttons, selection boxes, fillable fields, or any combination thereof that the user may answer, select, or input data into, for example by typed, stylus/touch-screen, oral, and/or written.

In an illustrative embodiment the mobile client device 102 may include one or more security features to prevent unauthorized users from using the mobile client device 102. The mobile client device 102 may require a user name and password, and/or other personal identification information, which can be used to identify and/or authenticate the user 104.

Although the mobile client device 102 is described above as being the Apple® iPad®, the mobile client device 102 may be a digital camera, a digital video recorder, or other mobile electronic communication device such as but not limited to a computer, a tablet computer, a smart phone, a personal digital assistant (PDA), and other mobile devices that can access, provide, transmit, receive, and modify information over wired or wireless networks, that contains the optical and image acquisition technology described above, and that is capable of receiving and using the laser measuring device described above. Further, the measurement module 108 may be platform agnostic and can be accessed by and run on various computing platforms.

Although the laser measurement devices 206, 302, and 1202 are described as plugging into the audio port 204 and being activated via an audio signal from the mobile client device 102, it should be appreciated by that those skilled in the art that the laser measurement devices 206, 302, and 1202 may be configured to plug into the mobile client device 102 using alternative means. Such alternative means may include, but are not limited to a universal serial bus (USB), and other means of the type. Further, although the laser measurement devices 206, 302, and 1202 are described as including two visible light, red dot low power lasers, it should be appreciated by that those skilled in the art that more than two lasers may be included, and that other types of lasers may be used instead of the visible light, red dot low power lasers.

Although the systems and methods disclosed herein may have been with reference to one of the laser measurement devices 206, 302, and 1202, it should be appreciated that any of the laser measurement devices 206, 302, and 1202 may be used in accordance with the systems and methods disclosed herein.

While the systems and methods have been described and illustrated in connection with certain embodiments, many variations and modifications will be evident to those skilled in the art and may be made without departing from the spirit and scope of the disclosure. The disclosure is thus not to be limited to the precise details of methodology or construction set forth above as such variations and modification are intended to be included within the scope of the disclosure. Moreover, unless specifically stated any use of the terms first, second, etc. do not denote any order or importance, but rather the terms first, second, etc. are merely used to distinguish one element from another.

What is claimed is:

1. A digital measurement system for optical applications, comprising:
   a mobile client device including a digital camera and an audio port;
   a laser measurement device including a laser and a magnetic card reader, said laser measurement device electrically connected to said audio port of said mobile client device; and
   said mobile client device configured to activate said laser in response to said digital camera being activated and receive an electrical signal from said magnetic card reader in response to said magnetic card reader reading a magnetic strip of a card.

2. The system of claim 1, wherein said laser of said laser measurement device includes a first laser and a second laser.

3. The system of claim 1, wherein said mobile client device is configured to transmit an audio signal to said laser of said laser measurement device.

4. The system of claim 3, wherein said audio signal activates said laser of said laser measurement device in response to said digital camera being activated.

5. The system of claim 1, wherein said laser measurement device includes a card slot proximal to said magnetic card reader.

6. The system of claim 1, wherein said magnetic card reader is configured to read a magnetic pattern of said magnetic strip of said card.

7. The system of claim 6, wherein said magnetic card reader is configured to convert said magnetic pattern to said electrical signal.

8. The system of claim 1, wherein said magnetic card reader is configured to output said electrical signal to said audio port of said mobile client device.

9. The system of claim 1, wherein said mobile client device is configured to convert said electrical signal to digital data representing information stored on said card.

10. The system of claim 9, wherein said mobile client device is configured to communicate said digital data to a credit card processing service.

11. A laser measurement device, comprising:
    a housing having a first side and an internal compartment;
    an aperture in said first side of said housing;
    a laser disposed in said internal compartment and in alignment with said aperture;
    control circuitry disposed in said internal compartment and electrically connected to said laser, said control circuitry configured to activate said laser in response to receiving an audio signal;
    a magnetic card reader disposed in said internal compartment; and
    a card slot in said housing proximal to said magnetic card reader.

12. The laser measurement device of claim 11, wherein said aperture includes a first aperture and a second aperture, and said laser includes a first laser in alignment with said first aperture and a second laser in alignment with said second aperture.

13. The laser measurement device of claim 11, wherein said housing includes supports extending from said housing and configured to couple said housing to a mobile client device.

14. The laser measurement device of claim 11, further comprising wiring configured to electrically connect said control circuitry to an audio port of a mobile client device.

15. The laser measurement device of claim 11, further comprising wiring configured to electrically connect said magnetic card reader to an audio port of a mobile client device.

16. The laser measurement device of claim 11, further comprising a calibration connector disposed in said internal compartment, said laser disposed in said calibration connector.

17. The laser measurement device of claim 16, wherein said calibration connector is configured to allow a user to calibrate a position of said laser.

18. The laser measurement device of claim 11, further comprising a power source disposed in said internal compartment and electrically connected to said control circuitry.

19. The laser measurement device of claim 11, wherein said housing includes a cover portion configured to enclose said internal compartment.

20. The laser measurement device of claim 19, wherein said cover portion is removable.

* * * * *